US 9,445,790 B2
(12) United States Patent
Zinn et al.

(10) Patent No.: US 9,445,790 B2
(45) Date of Patent: Sep. 20, 2016

(54) INSERTION DEVICE FOR PROVIDING FINE NEEDLE ASPIRATION AND CORE BIOPSY

(75) Inventors: Kenneth M. Zinn, Westport, CT (US); Mark Fisher, Sellersville, PA (US)

(73) Assignees: Medical Components, Inc., Harleysville, PA (US); Innovative Medical Devices, LLC., Westport, CT (US)

( * ) Notice: Subject to any disclaimer, the term of this patent is extended or adjusted under 35 U.S.C. 154(b) by 1282 days.

(21) Appl. No.: 13/336,482

(22) Filed: Dec. 23, 2011

(65) Prior Publication Data

US 2013/0165815 A1 Jun. 27, 2013

(51) Int. Cl.
*A61B 10/02* (2006.01)

(52) U.S. Cl.
CPC .... *A61B 10/0275* (2013.01); *A61B 2010/0208* (2013.01)

(58) Field of Classification Search
CPC .................. A61B 10/0275; A61B 2010/0208
See application file for complete search history.

(56) References Cited

U.S. PATENT DOCUMENTS

| | | | |
|---|---|---|---|
| 4,600,014 A * | 7/1986 | Beraha | 600/567 |
| 5,161,542 A | 11/1992 | Palestrant | |
| 5,313,958 A | 5/1994 | Bauer | |
| 5,511,556 A | 4/1996 | DeSantis | |
| 5,526,822 A * | 6/1996 | Burbank et al. | 600/567 |
| 5,817,033 A | 10/1998 | DeSantis et al. | |
| 5,916,175 A | 6/1999 | Bauer | |
| 5,951,489 A | 9/1999 | Bauer | |
| 6,358,217 B1 | 3/2002 | Bourassa | |
| 7,001,396 B2 * | 2/2006 | Glazier et al. | 606/108 |
| 7,018,343 B2 | 3/2006 | Plishka | |
| 7,766,843 B2 | 8/2010 | Voegele | |
| 8,002,713 B2 | 8/2011 | Heske et al. | |

(Continued)

FOREIGN PATENT DOCUMENTS

| | | |
|---|---|---|
| WO | 0224077 A1 | 3/2002 |
| WO | 2004045415 A1 | 6/2004 |

OTHER PUBLICATIONS

"Temno Evolution® biopsy needle—An evolution in design; A revolution in performance," Product Brochure, CareFusion, San Diego, CA, available at http://www.carefusion.com/pdf/Interventional_Specialties/Temno_Evolution_Brochure.pdf, last accessed Dec. 7, 2011, 4 pages.

(Continued)

*Primary Examiner* — Rene Towa
(74) *Attorney, Agent, or Firm* — Buchanan Ingersoll & Rooney PC

(57) ABSTRACT

An insertion device for taking samples within a body. The insertion device includes a trigger housing, an outer sheath assembly, a sampling device, and a resilient member. The trigger housing includes an interior channel in which the resilient member is disposed to urge the outer sheath assembly away from a proximal end of the trigger housing. The outer sheath assembly is disposed within the interior channel of the trigger housing. The outer sheath assembly includes a body and an outer sheath attached to a distal end of the body. The sampling device is removably disposed within the outer sheath assembly and the trigger housing. The sampling device may be a removable biopsy needle assembly which is used to cock the insertion device. The removable biopsy needle assembly may be removed from the insertion device and be replaced by a needle assembly for fine needle aspiration.

24 Claims, 12 Drawing Sheets

(56) References Cited

U.S. PATENT DOCUMENTS

2007/0106176 A1    5/2007  Mark et al.
2007/0208271 A1*   9/2007  Voegele .................. 600/564
2007/0239064 A1*  10/2007  Cicenas et al. ............ 600/566
2008/0294111 A1*  11/2008  Tal et al. ............... 604/165.01
2009/0326476 A1*  12/2009  Carlyon .................. 604/197

OTHER PUBLICATIONS

"Temno II® Biopsy Needles," Product Website, CardinalHealth, Dublin, OH, available at http://www.cardinal.com/us/en/distributedproducts/ASP/TS226.asp?cat=surgerycenter, last accessed Dec. 7, 2011, 3 pages.

* cited by examiner

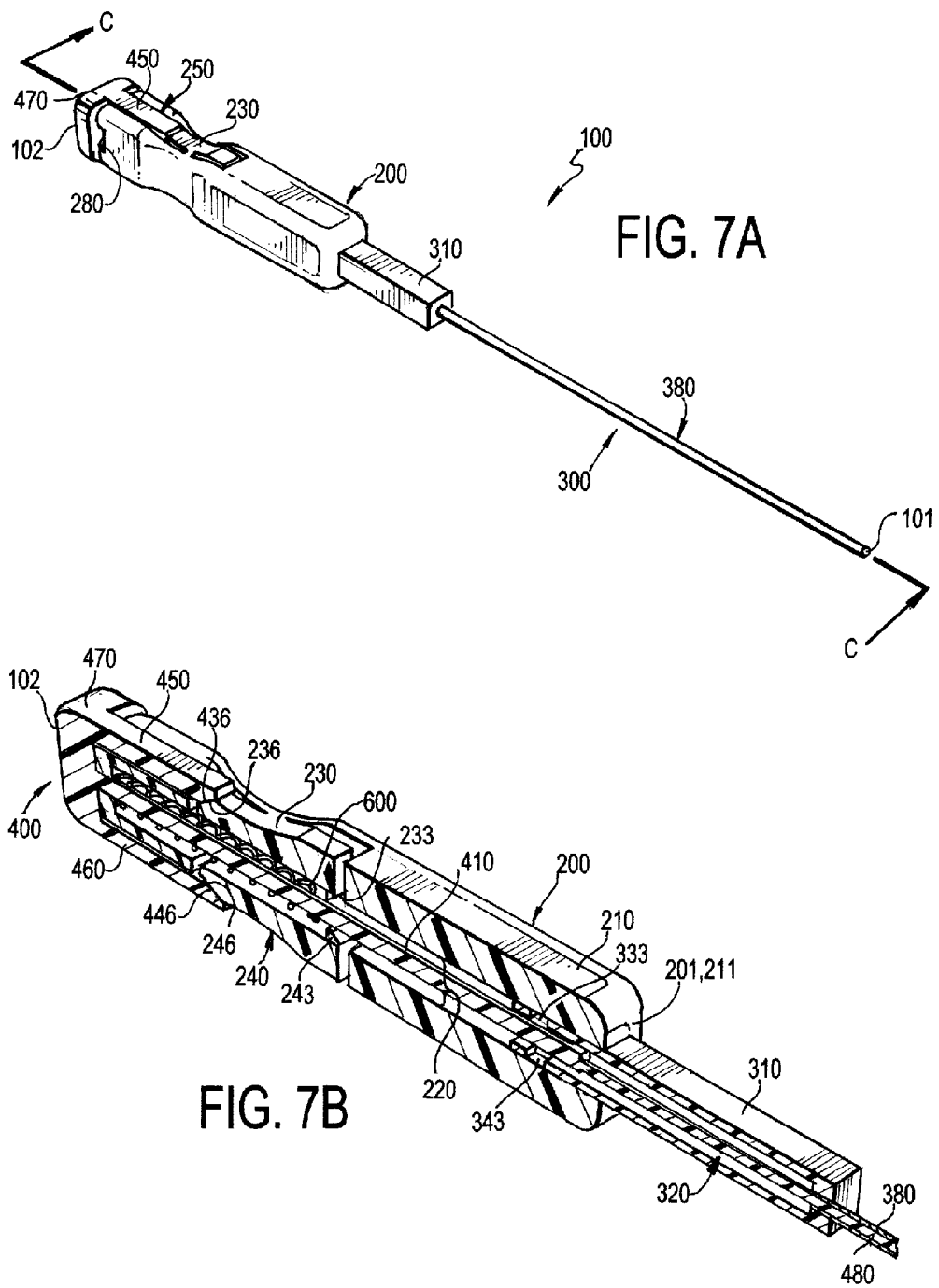

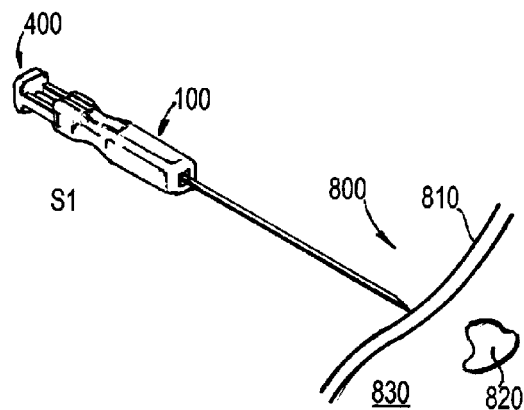
FIG. 8A
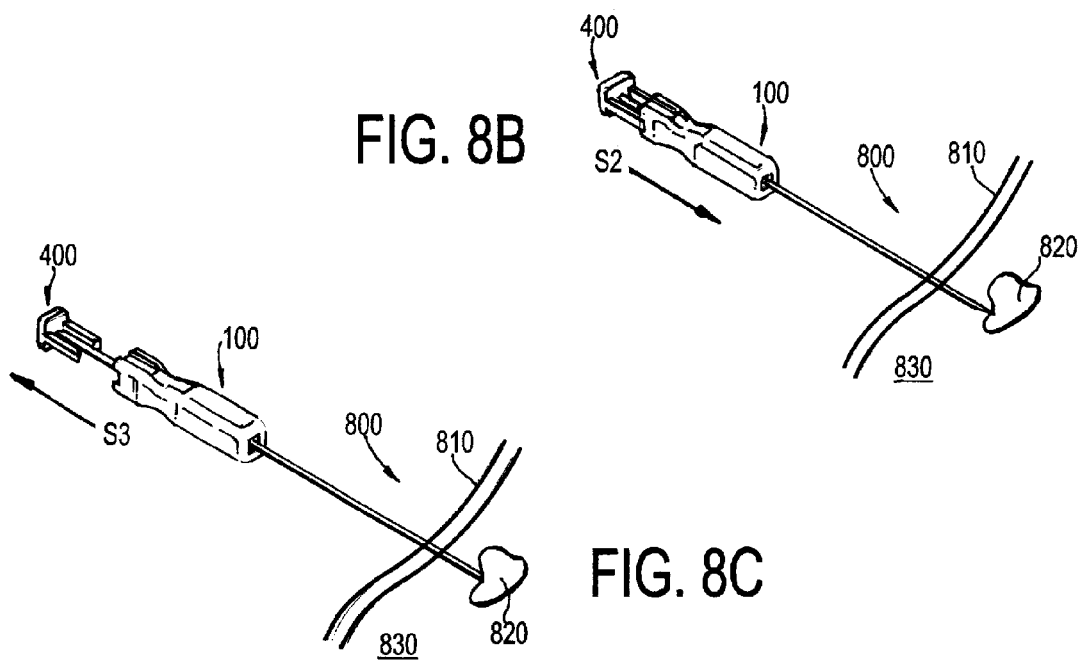
FIG. 8B
FIG. 8C
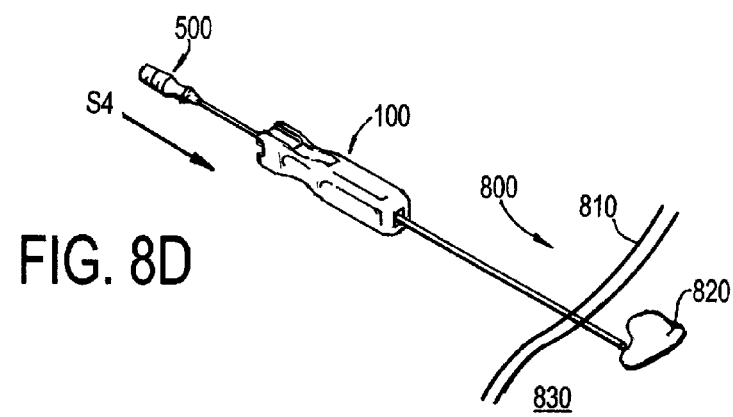
FIG. 8D

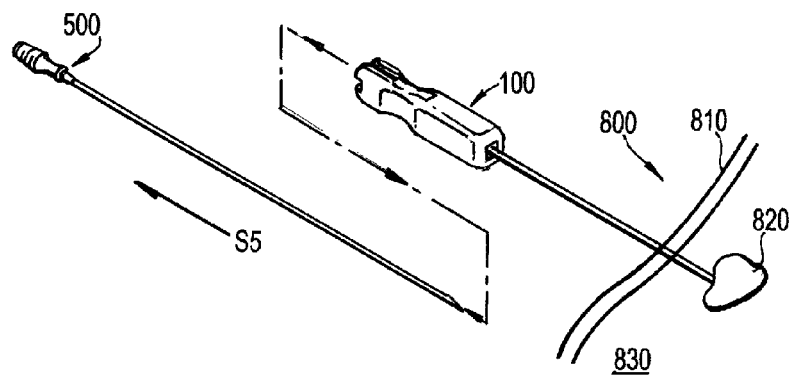
FIG. 8E
FIG. 8F
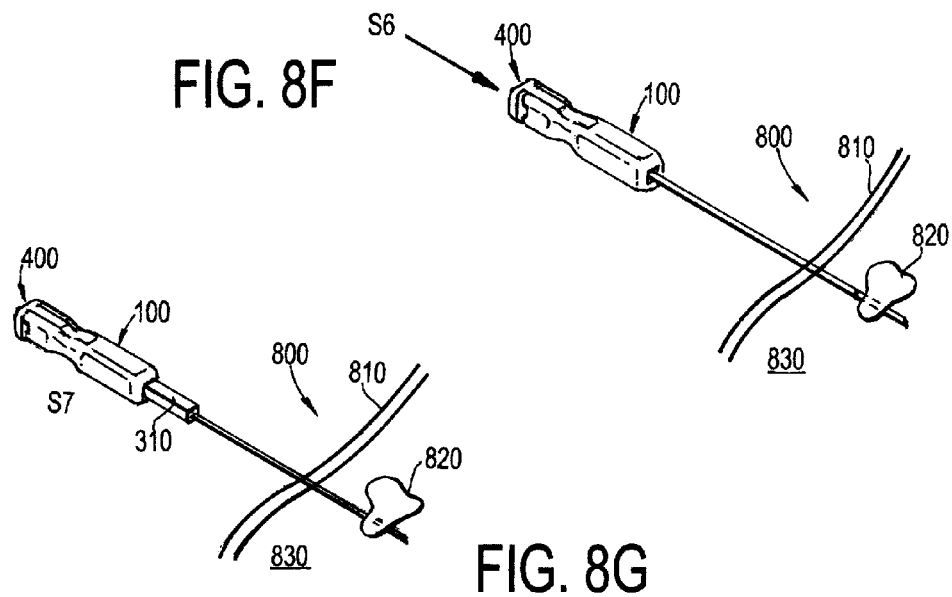
FIG. 8G
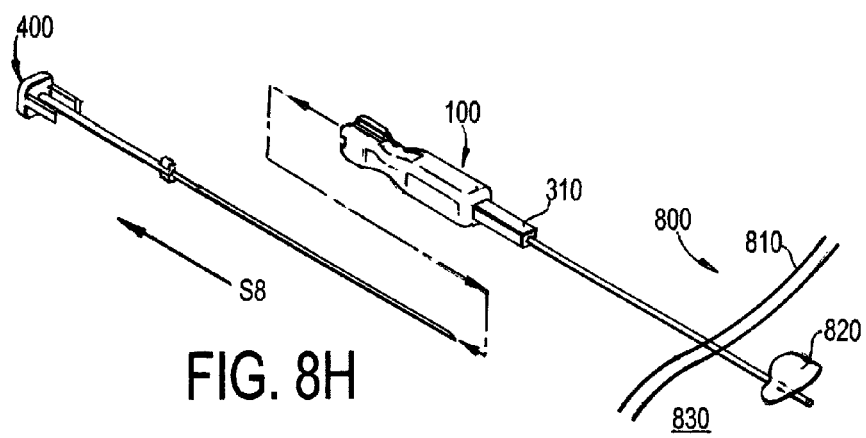
FIG. 8H

INSERTION DEVICE FOR PROVIDING FINE NEEDLE ASPIRATION AND CORE BIOPSY

FIELD OF THE INVENTION

The present invention relates, generally, to a device for providing fine needle aspiration and core biopsy and, more specifically, to a device configured to removably carry a first needle for fine needle aspiration and a second needle for obtaining a core biopsy.

BACKGROUND OF THE INVENTION

FIG. 10 illustrates a conventional biopsy device 1000 which includes an outer sheath assembly 1010 and an inner cannula assembly 1020. The outer sheath assembly 1010 includes an outer cannula 1012, a body 1014, and a handle 1016. A proximal opening 1018 is provided in the proximal end of the handle 1016.

The inner cannula assembly 1020 includes an inner cannula 1022 extending distally from an inner cannula locking hub 1024. A proximal opening 1026 is provided in the proximal end of inner cannula assembly 1020. The inner cannula assembly 1020 further includes a closed, distal tissue penetrating tip 1028, adapted for piercing tissue, and a side tissue sample port 1029 disposed proximally of the tip 1028. The sample port 1029 communicates with a central lumen extending the length of cannula 1022 to the proximal opening 1026.

The proximal opening 1018 of the outer sheath assembly 1010 allows for insertion of the inner cannula 1022 into the outer sheath assembly 1010. The relative position of the inner cannula 1022 to the outer sheath assembly 1010 can be maintained in a plurality of positions to provide a desired biopsy sampling mode.

The body 1014 further includes a biopsy method selection button 1017 and a release button 1019. The biopsy method selection button 1017 is used to select the desired biopsy sampling mode from the following: a fine needle aspiration mode of operation or a core sample mode of operation. In the fine needle aspiration mode of operation, a sample is withdrawn through the proximal opening 1026 via the sample port 1029 and the inner cannula 1022. In the core sample mode of operation, the release button 1019 is used to release the position of the outer cannula 1012 to obtain a core sample of tissue.

FIG. 10 illustrates the biopsy device 1000 in a position for obtaining a fine needle aspiration (FNA) sample through the proximal opening 1026 via the sample port 1029 and the inner cannula 1022. In this position, the outer cannula 1012 is partially retracted proximally relative to inner cannula 1022 by a distance less than the longitudinal length of the sample port 1029, in order to expose a portion, but not all of, the longitudinal length of the sample port 1029. This position is accomplished by pushing the selection button 1017 in a proximal direction.

In an insertion position, the outer cannula 1012 completely covers the sampling port 1029, thereby preventing tissue from entering the sample port 1029 during insertion or removal of the device 1000. In a core biopsy position, the outer cannula 1012 is retracted to a position in which the sampling port 1029 is fully exposed. Moving the selection button 1017 proximally causes the outer cannula 1012 to move proximally to fully expose the sample port 1029 in this position. In order to sever a core sample of tissue, the release button 1017 is depressed to cause the outer cannula 1012 to snap over the sample port 1029. As the outer cannula 1012 snaps over the sample port 1029, the outer cannula 1012 cuts through the tissue of interest, thereby severing any tissue disposed in the sample port 1029 to provide a core sample.

SUMMARY OF THE INVENTION

In accordance with an aspect of the present invention, there is provided an insertion device for taking samples within a body. The insertion device includes a trigger housing, an outer sheath assembly, and a resilient member. The trigger housing includes a proximal end, a distal end, and an interior channel in which the resilient member is disposed to urge the outer sheath assembly away from the proximal end of the trigger housing. At least a portion of the outer sheath assembly is slidably disposed within the interior channel of the trigger housing. The outer sheath assembly includes a body and an outer sheath attached to a distal end of the body. The outer sheath assembly is configured for removably receiving a sampling assembly.

In accordance with another aspect of the present invention, there is provided an insertion device for taking samples within a body. The insertion device includes a trigger housing, an outer sheath assembly, a removable biopsy needle assembly, and a resilient member. The trigger housing includes a proximal end, a distal end, and an interior channel in which the resilient member is disposed to urge the outer sheath assembly away from the proximal end of the trigger housing. At least a portion of the outer sheath assembly is slidably disposed within the interior channel of the trigger housing. The outer sheath assembly includes a body and an outer sheath attached to a distal end of the body. The removable biopsy needle assembly is removably disposed within the outer sheath assembly through the body of the outer sheath assembly, an opening in the body of the outer sheath assembly, and the outer sheath of the outer sheath assembly. The removable biopsy needle assembly is used to cock the insertion device. The removable biopsy needle assembly may be removed from the insertion device and be replaced by a needle assembly for fine needle aspiration.

In accordance with yet another aspect of the present invention, there is provided a method of inserting an insertion device into a body. The method includes steps of placing an insertion device in a first rotational position and inserting the insertion device into a body. The insertion device includes a trigger housing, an outer sheath assembly, a removable biopsy needle assembly, and a resilient member. The trigger housing includes a proximal end, a distal end, and an interior channel in which the resilient member is disposed to urge the outer sheath assembly away from the proximal end of the trigger housing. At least a portion of the outer sheath assembly is slidably disposed within the interior channel of the trigger housing. The outer sheath assembly includes a body and an outer sheath attached to a distal end of the body. The removable biopsy needle assembly is removably disposed within the outer sheath assembly through the body of the outer sheath assembly, an opening in the body of the outer sheath assembly, and the outer sheath of the outer sheath assembly. The removable biopsy needle assembly is used to cock the insertion device. The removable biopsy needle assembly may be removed from the insertion device and be replaced by a needle assembly for fine needle aspiration.

BRIEF DESCRIPTION OF THE DRAWINGS

For the purpose of illustration, there are shown in the drawings certain embodiments of the present invention. In the drawings, like numerals indicate like elements throughout. It should be understood that the invention is not limited to the precise arrangements, dimensions, and instruments shown. In the drawings:

FIG. 7A illustrates a perspective view of the insertion device in a decocked state after firing, in accordance with an exemplary embodiment of the present invention;

FIG. 7B illustrates a perspective view of a cross-section of the insertion device of FIG. 7A taken along a line C-C illustrated therein, in accordance with an exemplary embodiment of the present invention;

FIGS. 8A-8H illustrate steps of a method for inserting the insertion device of FIG. 1 into a patient and taking samples using the biopsy needle assembly and the needle for fine needle aspiration illustrated in FIG. 4, in accordance with an exemplary embodiment of the present invention;

DETAILED DESCRIPTION OF THE INVENTION

Figure 10:
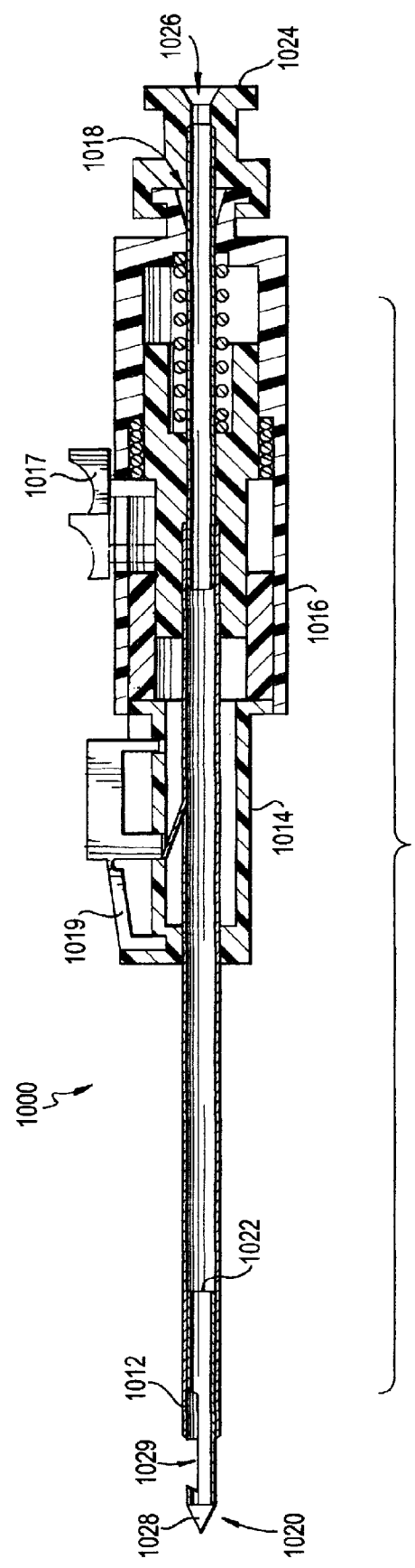
FIG. 10 illustrates a cross-sectional view of a conventional device for taking core biopsy and fine-needle aspiration samples.

The conventional biopsy device 1000 of FIG. 10 provides for a locking relationship between the outer sheath assembly 1010 and the inner cannula assembly 1020. FNA samples and core biopsies are taken without removing the inner cannula assembly 1020 from the outer sheath assembly 1010. In other words, the conventional biopsy device 1000 takes such FNA and core biopsy samples through a single inner cannula assembly 1020. Obtaining an FNA sample through the sample port 1029 of the inner cannula assembly 1020 may damage the cells obtained and distort the underlying tissue so that obtaining subsequent samples using image guidance, e.g. ultrasound, computed tomography (CT), and magnetic resonance imaging (MRI), may be more difficult. Additionally, because the inner cannula assembly 1020 stays within the outer sheath assembly 1010, a post-biopsy clip cannot be easily deployed through the device 1000. A second entry would be required. Thus, the locking relationship between the outer sheath assembly 910 and the inner cannula assembly 1020 is disadvantageous for performing both FNA samples and core biopsies.

By using the inner cannula assembly 1020 for FNA samples, the conventional biopsy device 1000 does not permit the medical practitioner to select the configuration of the FNA needle tip. In fact, as described above, FNA samples are taken via the sample port 1029. No FNA needle is even used. This may be disadvantageous as the medical practitioner may want to select the type of needle tip for FNA, depending on both the tissue being sampled and user preference. Examples of tips are Chiba, Franseen, and Wescott.

Additionally, the use of two user-operated buttons, the method selection button 1017 and the release button 1019, is disadvantageous. Because they are adjacent to one another, the medical practitioner may confuse the two buttons and operate one when the function of the other is desired. Further, by being deployed on the side of the device 1000, either of the buttons 1017 and 1019 may be operated accidentally. For example, during FNA, the medical practitioner may accidentally operate the release button 1019, which would cause the outer cannula 1021 to snap over the sample port 1029, thereby causing the FNA to terminate and thereby resulting in a non-desired core biopsy sample being taken.

Reference to the drawings illustrating various views of exemplary embodiments of the present invention is now made. In the drawings and the description of the drawings herein, certain terminology is used for convenience only and is not to be taken as limiting the embodiments of the present invention. The terms, "distal" and "proximal," refer, respectively, to directions away from and closer to the medical practitioner inserting the insertion device described herein into a patient. As used herein, the terms, "first" and "second," refer, respectively to "distal" and "proximal" where context permits. Furthermore, in the drawings and the description below, like numerals indicate like elements throughout.

Figure 1A:
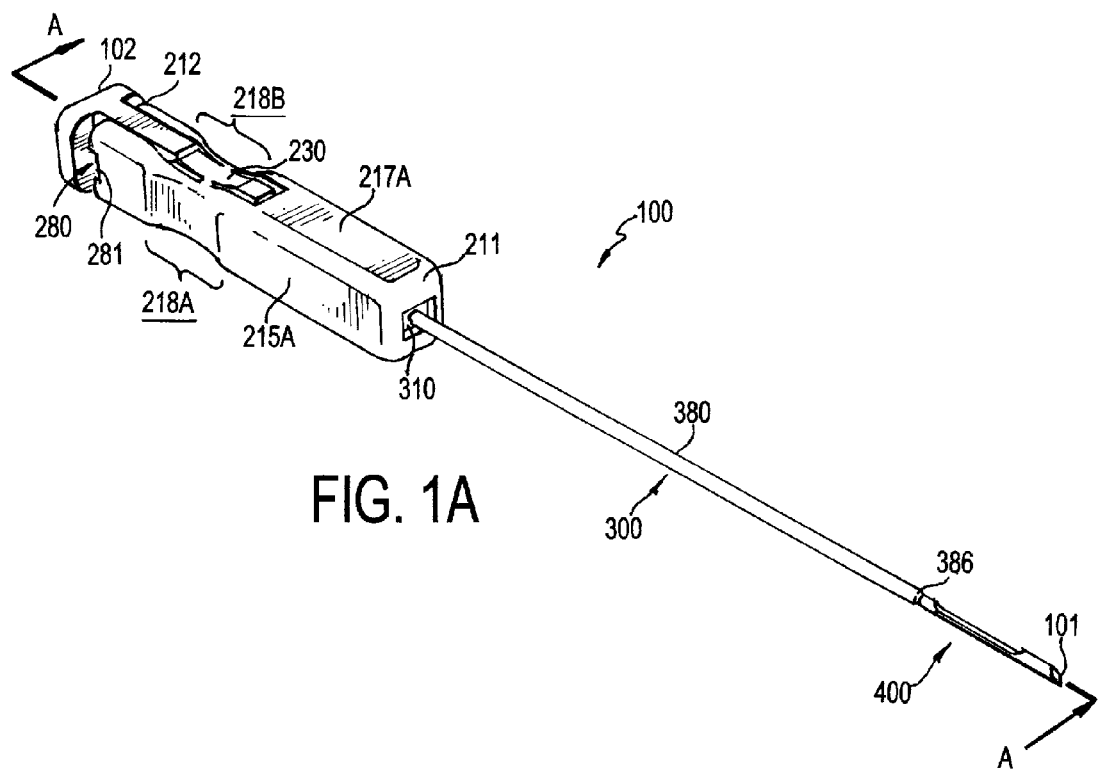
FIG. 1A illustrates a perspective view of an insertion device comprising a trigger housing, an outer sheath assembly, and a biopsy needle assembly, the insertion device in a cocked state ready for firing, in accordance with an exemplary embodiment of the present invention.

Referring now to FIG. 1A, there is illustrated an insertion device, generally designated as 100, in accordance with an exemplary embodiment of the present invention. The insertion device 100 has a distal end 101 and a proximal end 102 and comprises a trigger housing 200, an outer sheath assembly 300, and a resilient member 600 (illustrated in FIG. 1B). As illustrated, the insertion device 100 further comprises a biopsy needle assembly 400, which is removable from the insertion device 100. Because the biopsy needle assembly 400 is removable, the term "insertion device" may refer to the insertion device 100 including the biopsy needle assembly 400 or an FNA needle assembly 500 (illustrated in FIG. 4), or it may refer to the insertion device 100 with the biopsy needle assembly 400 or the FNA needle assembly 500 removed. In FIG. 1A, at least a portion of the biopsy needle assembly 400 is generally disposed within the outer sheath assembly 300, and at least a portion of the outer sheath assembly 300 is generally disposed within or through the trigger housing 200. In an exemplary embodiment, the resilient member 600 is a spring.

Figure 2A:
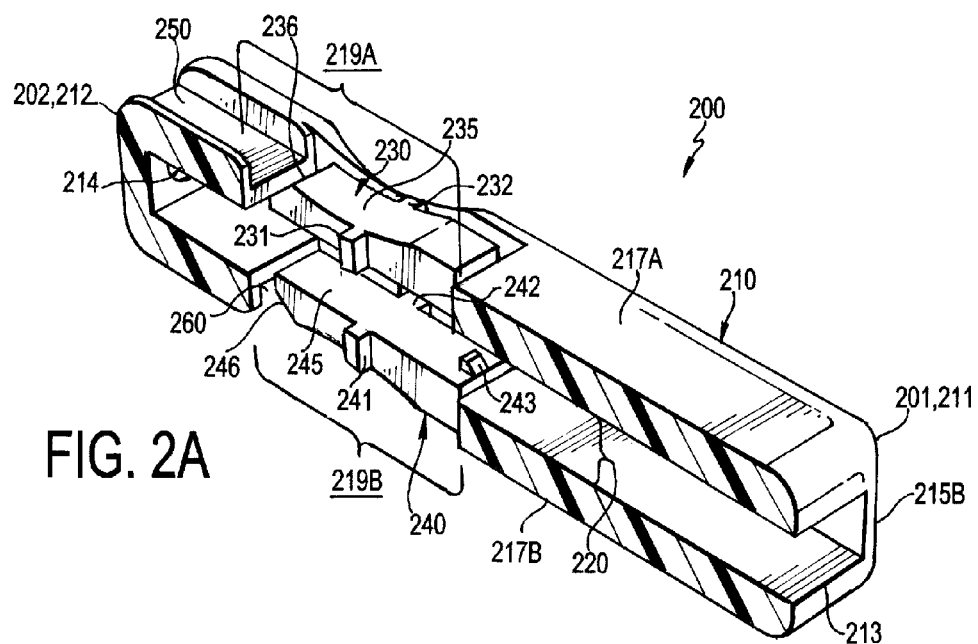
FIG. 2A illustrates a first perspective view of a cross-section of the trigger housing of FIG. 1A taken along an axis offset from the line A-A, in accordance with an exemplary embodiment of the present invention.
Figure 2B:
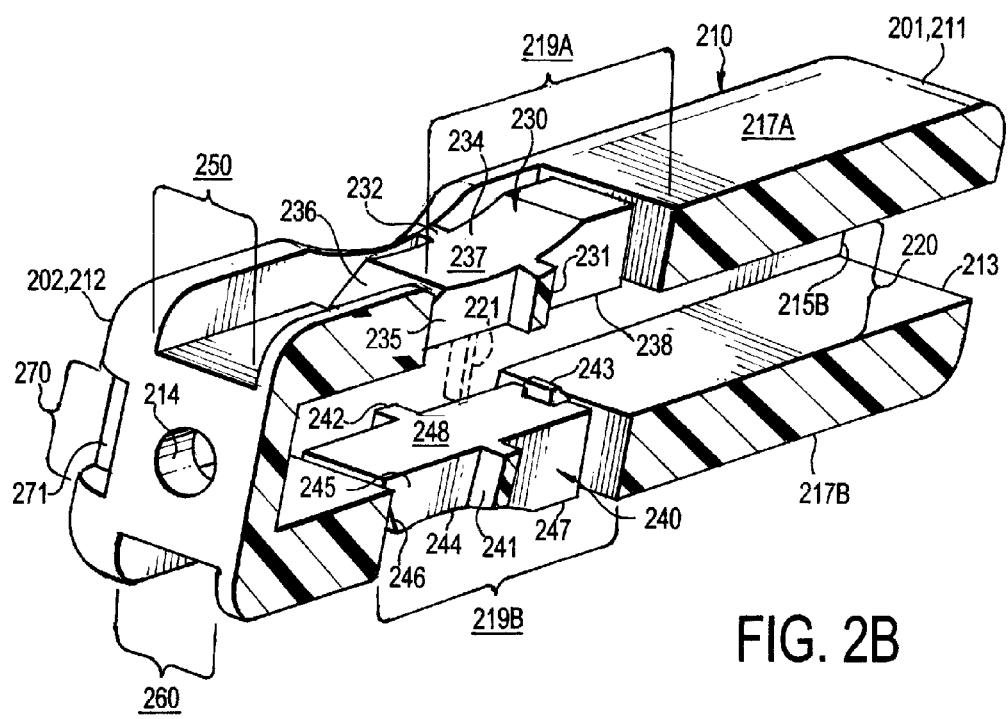
FIG. 2B illustrates a second perspective view of a cross-section of the trigger housing of FIG. 1A taken along an axis offset from the line A-A, in accordance with an exemplary embodiment of the present invention.

Illustrated in FIG. 2A is a first perspective view of a cross-section of the trigger housing 200 taken along an axis offset from a line A-A illustrated in FIG. 1A, in accordance with an exemplary embodiment of the present invention. Illustrated in FIG. 2B is a second perspective view of the cross-section of the trigger housing 200 taken along an axis offset from the line A-A illustrated in FIG. 1A, in accordance with an exemplary embodiment of the present invention. FIGS. 1A, 2A, and 2B are now described together.

The trigger housing 200 has a distal end 201 and a proximal end 202 and comprises a body 210 spanning the trigger housing 200 from the distal end 201 to the proximal end 202. The trigger housing 200, and more specifically the body 210, may be used as a handle by a medical practitioner using the insertion device 100 during a procedure to obtain one or more core biopsy samples and one or more FNA samples.

The body 210 has a distal end 211 and a proximal end 212. At the distal end 211, the body 210 comprises a distal opening 213, and at the proximal end 212, the body 210 comprises a proximal opening 214. The body 210 further includes a pair of opposing side walls 215A and 215B, a top wall 217A, and a bottom wall 217B. The walls 215 and 217 form an interior channel 220 disposed within the body 210. The distal opening 213 and the proximal opening 214 open to the interior channel 220. The trigger housing 200, and more specifically, the body 210, has a generally elongated rectangular (rectangular cuboid) shape. This shape facilitates using the trigger housing 200 as a handle.

The side walls 215A and 215B are generally planar, though they comprise respective indentations 218A and 218B. Likewise, the top wall 217A and the bottom wall 217B are generally planar. The top wall 217A, however, comprises a gap 219A disposed within an intermediate portion of the wall 217A and a channel 250 disposed at the proximal end 212 of the body 210. Similarly, the bottom wall 217B comprises a gap 219B disposed within an intermediate portion of the wall 217B and a channel 260 disposed at the proximal end 212 of the body 210.

Disposed within the gap 219A is a release rocker 230 which is resiliently connected to the side walls 215A and 215B by respective connectors 231 and 232. The release rocker 230 comprises a body 235 which comprises an outwardly facing trigger or press surface 236 disposed on a proximal end of the release rocker 230. Disposed within the gap 219B is a release rocker 240, which is resiliently connected to the side walls 215A and 215B by respective connectors 241 and 242. The release rocker 240 comprises a body 245 which comprises an outwardly facing trigger or press surface 246 disposed on a proximal end of the release rocker 240.

The release rocker 230 comprises an indentation 234 on an outer surface 237 thereof. The indentation 234 causes the profile of the top of the trigger housing 200 to have a shape similar to the side walls 215A and 215B (having respective indentations 218A and 218B) and also causes the release rocker 230 to be partially protected by the side walls 215A and 215B to prevent accidental actuation of the release rocker 230. The release rocker 240 also comprises an indentation 244 on an outer surface 247 thereof. The indentation 244 causes the profile of the bottom of the trigger housing 200 to have a shape similar to the side walls 215A and 215B (having respective indentations 218A and 218B) and also causes the release rocker 240 to be partially protected by the side walls 215A and 215B to prevent accidental actuation of the release rocker 240. Actuation of the release rockers 230 and 240 actuates the outer sheath assembly 300. Because the body 210 protects against accidental actuation of the release rockers 230 and 240, the insertion device 100 advantageously reduces the likelihood of accidental actuation of the outer sheath assembly 300. Actuation of the outer sheath assembly 300 is described below.

Disposed on an inner surface 238 of the release rocker 230 is a tab 233, and disposed on an inner surface 248 of the release rocker 240 is a tab 243. The tabs 233 and 243 extend inwardly into the interior channel 220 of the trigger housing 200. The tabs 233 and 243 serve to cock (releasably lock) the outer sheath assembly 300 with respect to the trigger housing 200. During actuation of the release rockers 230 and 240, the tabs 233 and 243 move outwardly away from the interior channel 220.

Figure 3A:
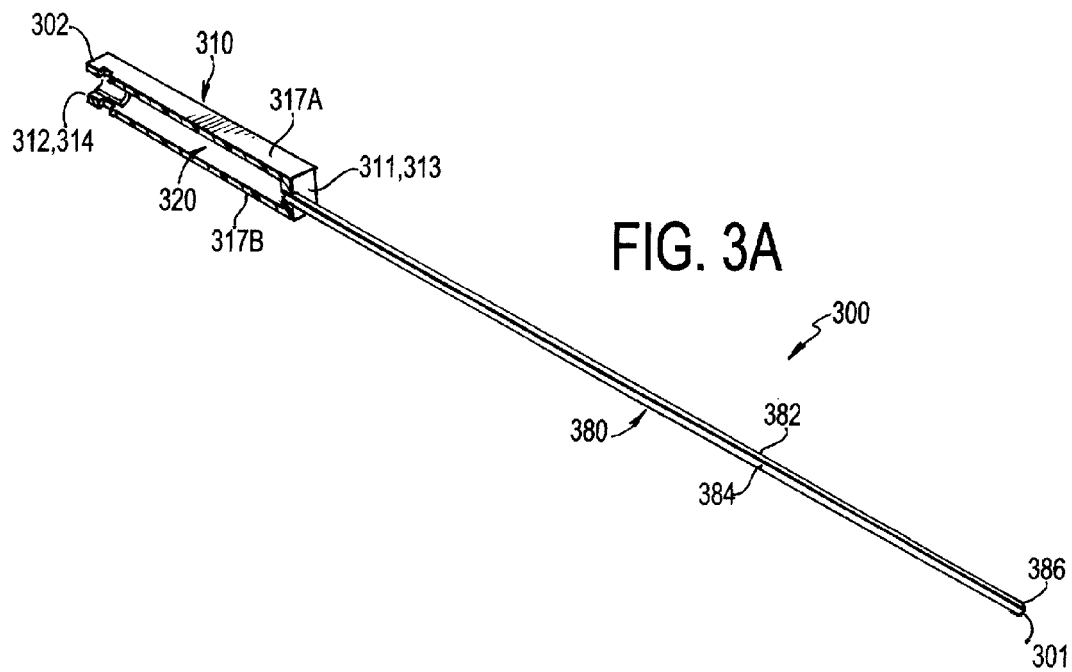
FIG. 3A illustrates a perspective view of a cross-section of the outer sheath assembly of FIG. 1A taken along the line A-A, the outer sheath assembly comprising a body and a cannula, in accordance with an exemplary embodiment of the present invention.
Figure 3B:
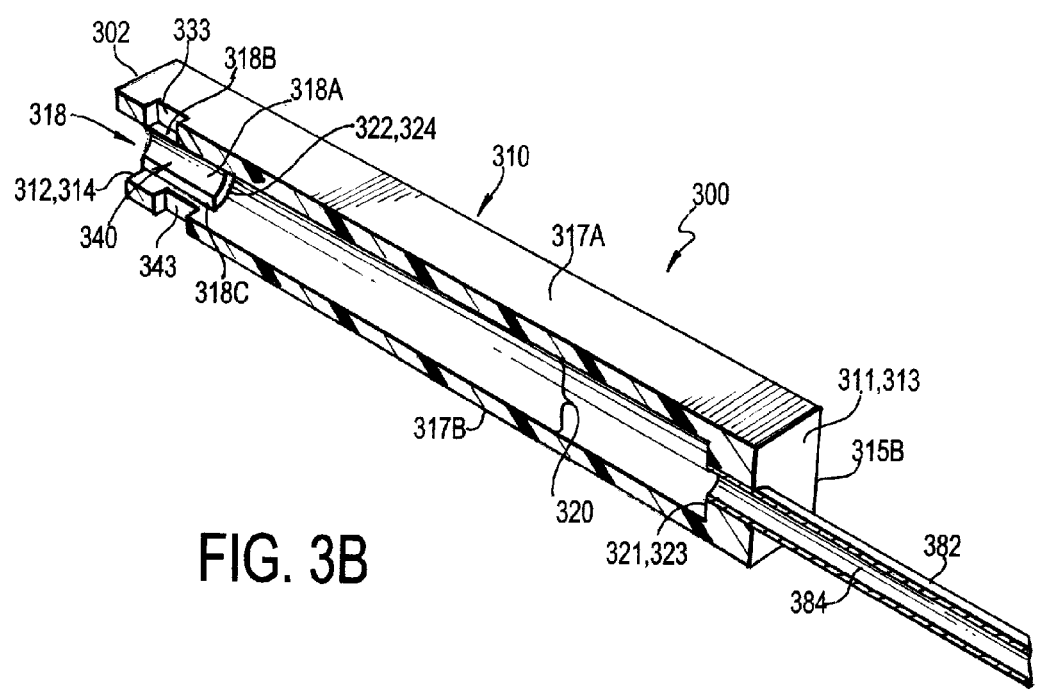
FIG. 3B illustrates a close-up view of the body of the outer sheath assembly illustrated in FIG. 3A in cross-section, in accordance with an exemplary embodiment of the present invention.

Illustrated in FIG. 3A is a perspective view of a cross-section of the outer sheath assembly 300 taken along the line A-A of FIG. 1A, in accordance with an exemplary embodiment of the present invention. FIG. 3B illustrates a close-up view of a portion of the perspective view of the cross-section of FIG. 3A, in accordance with an exemplary embodiment of the present invention. FIGS. 3A and 3B are now described together.

The outer sheath assembly 300 has a distal end 301 and a proximal end 302. Disposed at the proximal end 302 of the outer sheath assembly is a body 310 having a distal end 311 and a proximal end 312. The body 310 comprises side walls 315A (illustrated in FIG. 3C) and 315B, a top wall 317A, and a bottom wall 317B. Disposed at the distal end 311 of the body 310 is a distal wall 313, and disposed at the proximal end 312 of the body 310 is a proximal wall 314 comprising a proximal opening 318. The body 310 has a generally elongated rectangular (rectangular cuboid) shape as the side walls 315A and 315B, the top wall 317A, and the bottom wall 317B are generally planar. The walls 315 and 317 form an interior channel 320 disposed within the body 310.

Connected to the distal end 311 of the body 310 is an outer sheath 380 comprising a cannula 382 and an internal lumen 384. The outer sheath 380 extends from the distal end 311 of the body 310 to the distal end 301 of the outer sheath assembly 300. The distal end of the outer sheath 380 at the distal end 301 of the outer sheath assembly 300 comprises a bevel 386 for shearing off a core biopsy sample when the outer sheath assembly 300 is actuated.

The cannula 382 of the outer sheath 380 pierces the distal wall 313 of the body 310 so that the internal lumen 384 opens to the interior channel 320. The proximal opening 318 also opens to the interior channel 320. The proximal opening 318 is formed in the proximal wall 314 and comprises a center channel 318A, a top keyway 318B, and a bottom keyway 318C.

The interior channel 320 has a distal end 321 and a proximal end 322. The distal end 321 of the interior channel 320 comprises a distal stop surface 323, and the proximal end 322 of the interior channel 320 comprises a proximal stop surface 324. The distal stop surface 323 is formed by the distal wall 313. The proximal stop surface 324 is formed by a channel protrusion 330 and a channel protrusion 340, both of which extend into the interior channel 320 from the proximal wall 314. In an exemplary embodiment, the channel protrusions 330 and 340 are formed integrally with the proximal wall 314. In the exemplary embodiment illustrated in FIGS. 3A and 3B, each of the channel protrusions 330 and 340 has an elongated C shape.

The top wall 317A of the body 310 includes a slot 333 for receiving the tab 233, and the bottom wall 317B of the body 310 includes a slot 343 for receiving the tab 243. The body 310 of the outer sheath assembly is configured and sized to be received within the interior channel 220 of the trigger housing 200. The tab 233 of the release rocker 230 is configured to extend within the slot 333, and the tab 243 of the release rocker 240 is configured to extend within the slot 343, when the outer sheath assembly 300 is in position in preparation for firing. In an exemplary embodiment, the slot 333 passes through an entire width of the top wall 317A, and the slot 343 passes through an entire width of the bottom wall 317B. In an alternative exemplary embodiment, the slots 333 and 343 extend only partially through the respective walls 317A and 317B. In such embodiment, the slots 333 and 343 are recesses within the inner surfaces of the respective top wall 317A and bottom wall 317B.

In the exemplary embodiment illustrated in FIGS. 3A and 3B, the interior channel 320 and the inner lumen 384 both have cross-sections having respective circular shapes, and the body 310 has a generally elongated rectangular (rectangular cuboid) shape. The size and shape of the body 310 is selected so that the body 310 may be slidably fit into the interior channel 220 of the trigger housing 200. Thus, the interior channel 220 of the trigger housing 200 has a generally elongated rectangular (rectangular cuboid) shape configured to slidably receive the body 310. Other exemplary embodiments of the insertion device 100 having elongated circular shapes for the body 310 and the interior channel 220, for example, are also contemplated.

Figure 3C:
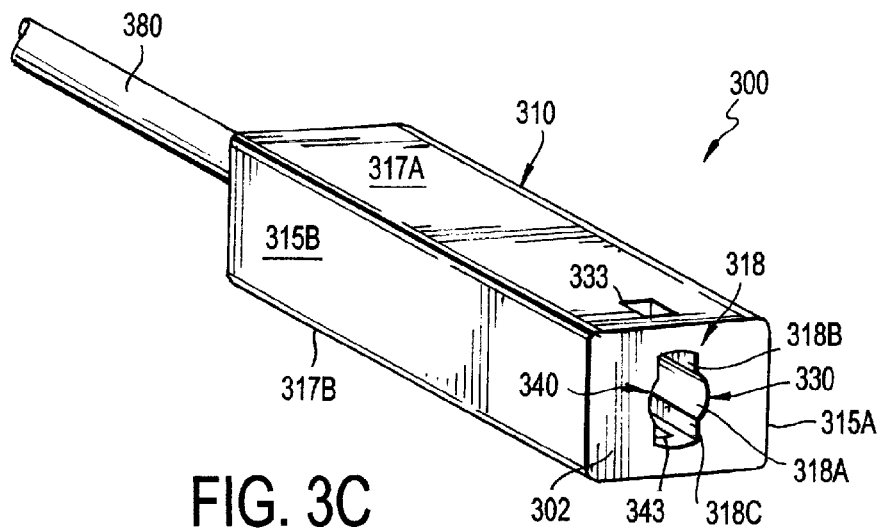
FIG. 3C illustrates a perspective view of the body of the outer sheath assembly of FIG. 1A, in accordance with an exemplary embodiment of the present invention.

FIG. 3C illustrates a perspective view of the proximal end 302 of the outer sheath assembly 300, in accordance with an exemplary embodiment of the present invention. As seen in the figure, the protrusions 330 and 340 protrude inwardly into the interior channel 320 and are generally C-shaped. The result is that the cross-section of the proximal opening 318 is smaller than the cross-section of the interior channel 320. The shape of the cross-section of the proximal opening 318 is also different from the cross-section of the interior channel 320.

Figure 4:
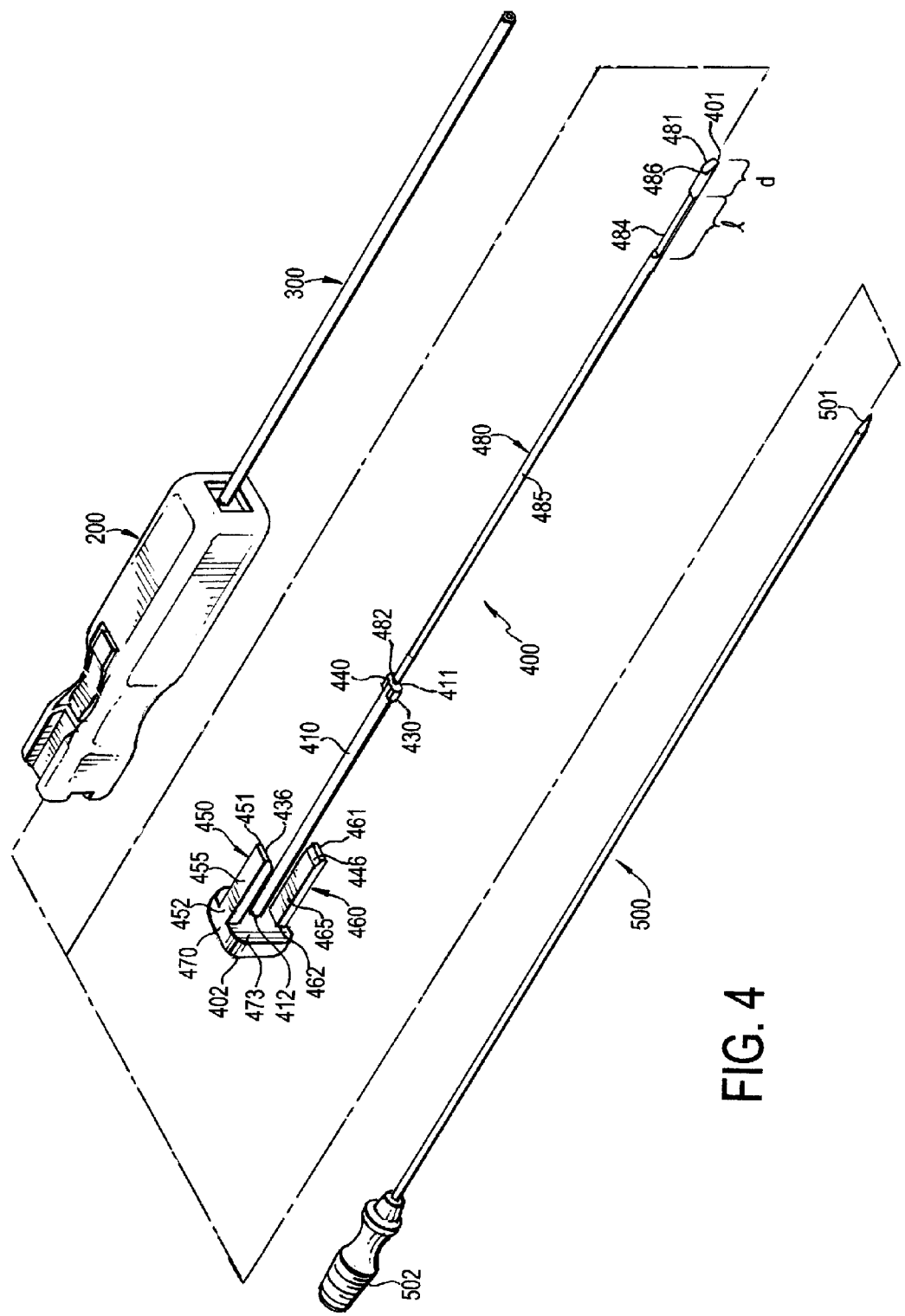
FIG. 4 illustrates the insertion device of FIG. 1 in which the biopsy needle assembly of FIG. 1 and a needle for fine needle aspiration have been removed from the insertion device, in accordance with an exemplary embodiment of the present invention.

Referring now to FIG. 4, there are illustrated a biopsy needle, generally designated as 400, and a needle for fine needle aspiration (FNA), generally designated as 500, in accordance with an exemplary embodiment of the present invention. The biopsy needle 400 and the FNA needle 500 are both examples of sampling assemblies configured for use with the embodiments of the insertion device 100 described herein. It is to be understood that any instrument for sampling fluids and/or tissue within a body, as known in the art, may be used as a sampling assembly in place of the FNA needle 500. It is to be understood that such instrument should be appropriately sized to be inserted into the insertion device 100 via the proximal opening 214 and through the inner lumen 384 of the outer sheath 380, as the FNA needle 500 is configured to be.

FIG. 4 also illustrates a portion (the body 310) of the outer sheath assembly 300 mounted within the trigger housing 200 in a position in which the tabs 233 and 243 are respectively disposed within the slots 333 and 343. Thus, FIG. 4 illustrates the outer sheath assembly 300 in a cocked state ready for firing. The biopsy needle assembly 400 and the FNA needle assembly 500 are illustrated removed from the outer sheath assembly 300 for clarity. They may be loaded into the outer sheath assembly 300 in the directions indicated by the arrows in FIG. 4 and removed in an opposite direction.

The biopsy needle assembly 400 has a distal end 401 and a proximal end 402 and comprises a sliding mount 410 and a base plate 470 disposed at the proximal end 402 of the biopsy needle assembly 400. The sliding mount 410 has a distal end 411 and a proximal end 412.

The biopsy needle assembly 400 also comprises a biopsy needle 480 having a distal end 481 and a proximal end 482. The proximal end 482 of the biopsy needle 480 is connected to the distal end 411 of the sliding mount 410 and extends distally toward the distal tip 401 of the biopsy needle device 400. The proximal end 412 of the sliding mount 412 is connected to the base plate 470.

The biopsy needle 480 comprises a beveled tip 486 disposed at the distal end 481. The biopsy needle 480 further comprises a body 485, which includes a notch 484 offset from the distal end 481. The notch 484 is a length l of material removed from the body 485 and is offset from the beveled tip 486 by a distance d. The body 485 of the needle 480 has a generally circular shape, which is sized to slidingly fit through the inner lumen 384 of the outer sheath 380. Thus, the shape of the notch 484 is semi-circular.

Figure 5:
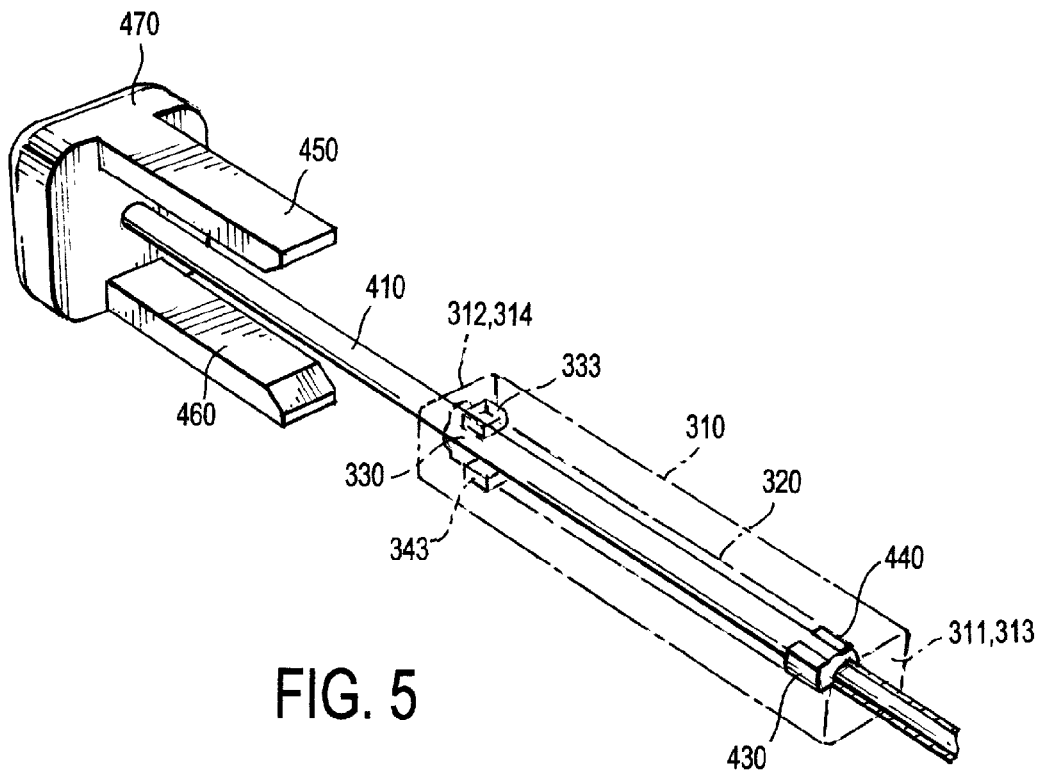
FIG. 5 illustrates a perspective skeleton view of the biopsy needle assembly disposed within the body of the outer sheath assembly, in accordance with an exemplary embodiment of the present invention.

The sliding mount 410 comprises a cross-section that is larger than a cross-section of the body 485 of the biopsy needle 480. Disposed on the sliding mount 410 at the distal end 411 thereof are two keys 430 and 440. Taken together, the keys 430 and 440 are greater in diameter than the diameter of the lumen 384 of the outer sheath 380 and the diameter of the center channel 318A of the proximal opening 318 of the body 310, but they are small in diameter than the interior channel 320 of the body 310 within which they are configured to slide distally and proximally. FIG. 5 illustrates a perspective view of the keys 430 and 440 disposed within the interior channel 320 of the body 310, in accordance with an exemplary embodiment of the present invention. FIG. 5 illustrates the body 210 as a skeleton so that the keys 430 and 440 are visible.

The size of the keys 430 and 440 relative to the proximal opening 318 causes the keys 430 and 440 to abut the proximal stop surface 324 during cocking of the insertion device 100 and after firing. The size of the keys 430 and 440 allows a medical practitioner to pull the outer sheath 300 assembly toward the proximal end 202 of the trigger housing 200 to cock the insertion device 200. Thus, during cocking of the outer sheath assembly 300, the keys 330 and 340 pull against the proximal stop surface 324 to move the outer sheath assembly 300 into the trigger housing 200 so that the tabs 233 and 243 engage the slots 333 and 343. The size of the keys 430 and 440 also prevents the outer sheath assembly 300 from exiting the trigger housing 200 at the distal end 201 after firing because the stop surface 324 runs into the keys 430 and 440 after firing. In an exemplary embodiment of the insertion device 200, to prevent the outer sheath assembly 300 from unwanted proximal movement beyond its position relative to the trigger housing 200 when cocked, the trigger housing 200 may include at least one inwardly projecting stop surface 221 (illustrated in FIG. 2B) within the interior channel 220 to abut the proximal wall 314 of the body 310 when the insertion device 100 is cocked and/or being inserted.

The base plate 470 is attached to the proximal end 412 of the sliding mount 410 and comprises a generally planar inner surface 473 from which generally parallel arms 450 and 460 extend. The arm 450 comprises a distal end 451, a proximal end 452, and a body 455 therebetween. The arm 460 comprises a distal end 461, a proximal end 462, and a body 465 therebetween. The proximal end 452 of the arm 450 is attached to the inner surface 473 of the base plate 470, and the proximal end 462 of the arm 460 is attached to the inner surface 473 of the base plate 470. The distal end 451 of the arm 450 comprises an inwardly facing push surface 436 for engaging and pressing against the trigger/press surface 236 of the release rocker 230 during firing. The distal end 461 of the arm 460 comprises an inwardly facing push surface 446 for engaging and pressing against the trigger/press surface 246 of the release rocker 240 during firing. The arm 450 is sized to be slidable through the channel 250 so that the push surface 436 may engage the trigger/press surface 236 during firing of the outer sheath assembly 300, and the arm 460 is sized to be slidable through the channel 260 so that the push surface 446 may engage the trigger/press surface 246 during firing of the outer sheath assembly 300.

The arms 450 and 460 are also used during insertion of the insertion device 100 into a patient. As seen in FIGS. 1A and 2B, the trigger housing 200 comprises a pair of recesses 270 and 280 disposed on opposite sides of the trigger housing 200 at its proximal end 202. Specifically, the side wall 215A includes the recess 280 having a push surface 281 at the proximal end 212 of the body 210, and the side wall 215B comprises the recess 270 having a push surface 271 at the proximal end 212 of the body 210. The recesses 270 and 280 are sized to respectively receive the distal ends 461 and 451 of the arms 460 and 450 during insertion of the outer sheath assembly 300. Specifically, during insertion, the medical practitioner presses the base plate 470 of the biopsy needle assembly 400 toward the distal end 101 of the insertion device 100. The distal end 451 of the arm 450 presses against the push surface 281 of the recess 280, and the distal end 461 of the arm 460 presses against the push surface 271 of the recess 270 to push the trigger housing 200 when the base plate 470 is pushed. Because the outer sheath assembly 300 engages the trigger housing 200, the outer sheath assembly 300 is also pushed. Thus, pushing on the base plate 470 pushes the entire insertion device 100. In the embodiment in which the trigger housing 200 includes the at least one inwardly projecting stop surface 221, the at least one inwardly projecting stop surface 221 also assists in translating the force applied to the base plate 470 to the outer sheath assembly 300 during insertion.

With reference to FIGS. 2B, 3C and 4, the shape of the proximal opening 318 is similar to the shape of the cross-section of the sliding mount 410 through the keys 430 and 440. The proximal opening 318 is sized to allow the keys 430 and 440 to respectively slide through the keyways 318C and 318B during removal of the biopsy needle assembly 400 from the trigger housing 200 and the outer sheath assembly 300. The center channel 318A of the proximal opening 318 is sized to accommodate movement and withdrawal of the sliding mount 410 of the biopsy needle assembly 400. The proximal opening 214 is sized to allow the keys 430 and 440 to respectively slide therethrough during removal of the biopsy needle assembly 400 from the trigger housing 200.

Figure 6A:
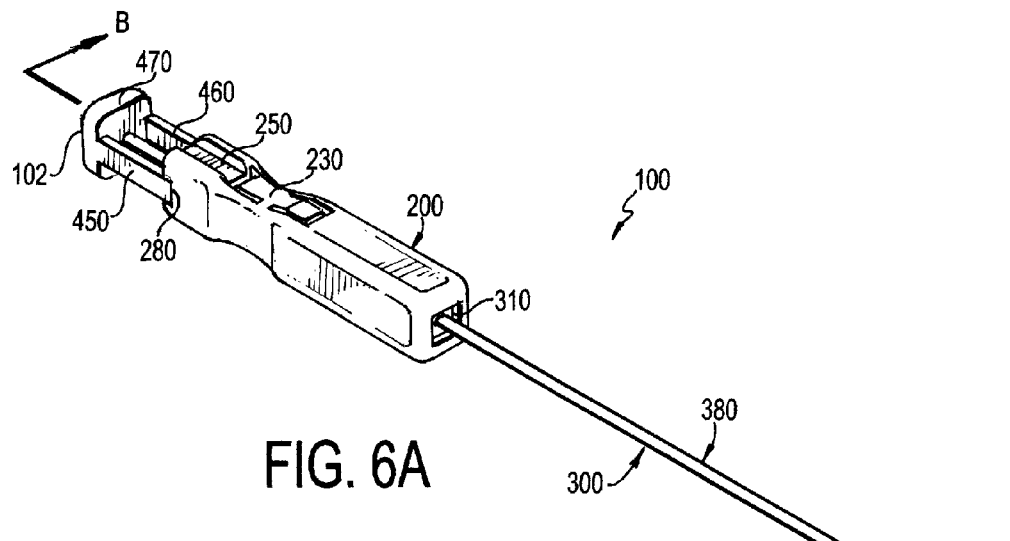
FIG. 6A illustrates a perspective view of the insertion device in a cocked state for insertion, in accordance with an exemplary embodiment of the present invention.
Figure 6B:
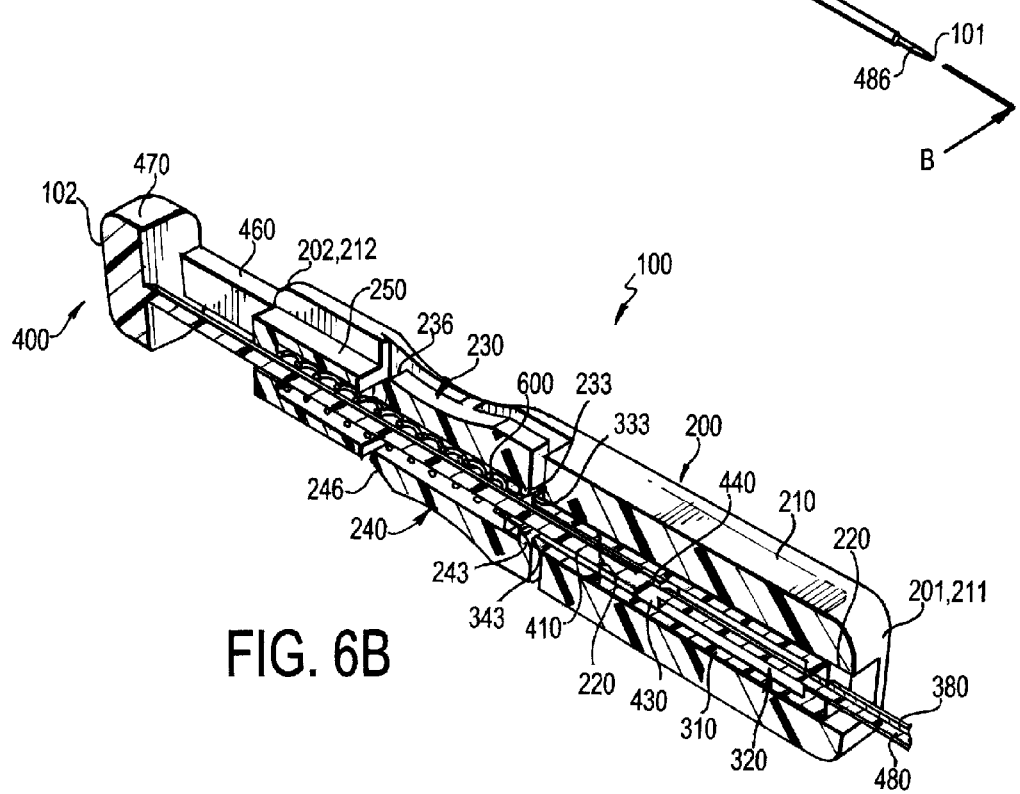
FIG. 6B illustrates a perspective view of a cross-section of the insertion device of FIG. 6A taken along a line B-B illustrated therein, in accordance with an exemplary embodiment of the present invention.

Illustrated in FIG. 6A is a perspective view of the insertion device 100 in a cocked state positioned for insertion, in accordance with an exemplary embodiment of the present invention. FIG. 6B illustrates a perspective view of a cross-section of the insertion device 100 taken along a line B-B illustrated in FIG. 6A. As shown in these figures, when the insertion device 100 is positioned for insertion, the outer sheath 380 covers the notch 484 of the biopsy needle 480 but does not cover the beveled tip 486, and the body 310 of the outer sheath assembly 300 is held within the trigger housing 200.

The outer sheath 380 covers the notch 484 of the biopsy needle 480 because the biopsy needle assembly 400 is offset proximally when in the position for insertion by virtue of the base plate 470 being separated from the proximal end 212 of the body 210 of the trigger housing 200. This offset is maintained and determined by the arms 450 and 460 engaging with their respective push surfaces 281 and 271 of the respective recesses 280 and 270 rather than residing with their respective channels 250 and 260. By covering the notch 484, the outer sheath 380 prevents unwanted tissue from entering the notch 484 during insertion. The beveled tip 486 remains exposed as it provides for penetration of tissue. Thus, because the outer sheath 380 covers the notch 484 of the biopsy needle 480, the insertion device 100 is in a position ready for insertion (or already is in the process of insertion or has been inserted).

As also seen in these figures, the body 310 of the outer sheath assembly 300 is fully disposed within the interior channel 220 of the trigger housing 200 when the insertion device 100 is cocked. The insertion device 100 maintains the body 310 in this position by virtue of the tabs 233 and 243 of the respective release rockers 230 and 240 residing within the respective slots 333 and 343 in the body 310 of the outer sheath assembly 300. Additionally, the distal ends 451 and 461 of respective arms 450 and 460 are disposed within the recesses 270 and 280, respectively. Because the tabs 233 and 243 are engaged with the respective slots 333 and 343, the insertion device 100 is cocked.

FIG. 6B illustrates the relative positions of the trigger housing 200, the outer sheath assembly 300, and the biopsy needle assembly 400 when the insertion device 100 is cocked and positioned for insertion. The figure also illustrates that the resilient member 600 is disposed within the trigger housing 200 about the sliding mount 410 of the biopsy needle assembly 400 between the proximal end 212 of the trigger housing 200 and the proximal wall 314 of the body 310 of the outer sheath assembly 300. The resilient member 600 urges the outer sheath assembly 300 away from the proximal end 212 of the trigger housing 200, i.e., away from the proximal end 102 of the insertion device 100. When the insertion device 100 is cocked, as it is in FIG. 6B, in the embodiment in which the resilient member 600 is a spring, the spring 600 is compressed, so that if it were released, the outer sheath assembly 300 would fire by moving away from the proximal end 102 of the insertion device 100.

Figure 1B:
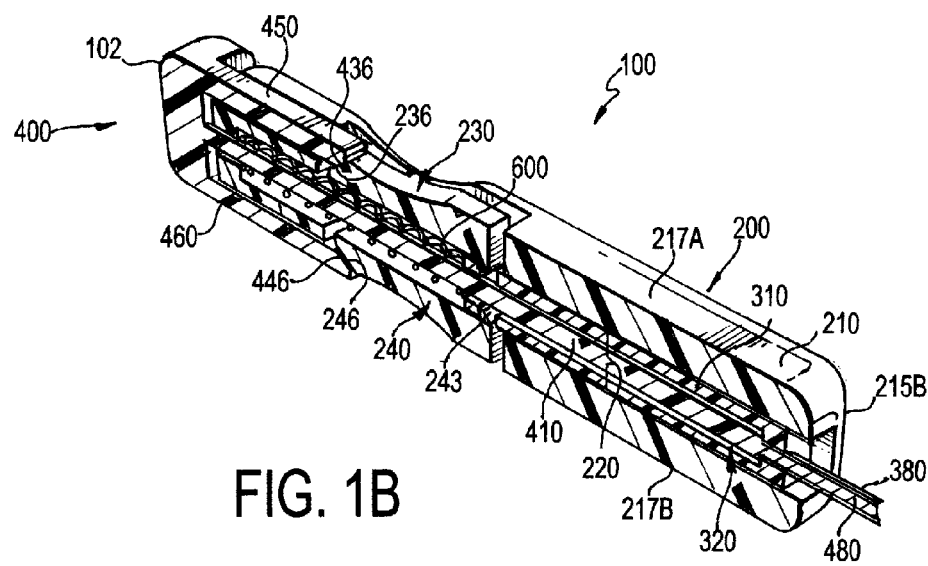
FIG. 1B illustrates a perspective view of a cross-section of the insertion device of FIG. 1A taken along a line A-A illustrated therein, in accordance with an exemplary embodiment of the present invention.

Referring again to FIG. 1A, there is illustrated a perspective view of the insertion device 100 in a cocked state positioned for firing, in accordance with an exemplary embodiment of the present invention. FIG. 1B illustrates a perspective view of a cross-section of the insertion device 100 taken along the line A-A illustrated in FIG. 1A. As shown in these figures, when the insertion device 100 is positioned for firing, the outer sheath 380 does not cover the notch 484 of the biopsy needle 480, and the body 310 of the outer sheath assembly 300 is held within the trigger housing 200.

The outer sheath 380 does not cover the notch 484 of the biopsy needle 480 because the biopsy needle assembly 400 is not offset proximally when in the position for firing by virtue of the base plate 470 being adjacent to the proximal end 212 of the body 210 of the trigger housing 200. There is no offset because the arms 450 and 460 are respectively disposed within the channels 250 and 260 of the trigger housing 200. Thus, because the outer sheath 380 does not cover the notch 484 of the biopsy needle 480, the insertion device 100 is in a position ready for firing to collect a core biopsy sample.

As with FIGS. 6A and 6B, the insertion device 100 shown in FIGS. 1A and 1B is cocked because the tabs 233 and 243 are engaged with the respective slots 333 and 343. Different from FIGS. 6A and 6B, the insertion device 100 shown in FIGS. 1A and 1B is in a position for firing because the push surface 436 of the arm 450 is adjacent to the trigger/press surface 236 of the release rocker 230, and the push surface 446 of the arm 460 is adjacent to the trigger/press surface 246 of the release rocker 240. Further movement of the base plate 470 toward the distal end 101 of the insertion device 100 would trigger the outer sheath assembly 300.

Illustrated in FIG. 7A is a perspective view of the insertion device 100 in a decocked state following firing, in accordance with an exemplary embodiment of the present invention. FIG. 7B illustrates a perspective view of a cross-section of the insertion device 100 taken along a line C-C illustrated in FIG. 7A. As shown in these figures, when the insertion device 100 has been fired, the outer sheath 380 covers the notch 484 of the biopsy needle 480 because the outer sheath assembly 300 has moved toward the distal end 101 of the insertion device compared to its position in FIGS. 1A, 1B, 6A, and 6B. Additionally, the body 310 of the outer sheath assembly 300 is partially disposed outside the trigger housing 200 but has been prevented from moving further away from the proximal end 102 of the insertion device 100 because the proximal stop surface 324 of the interior channel 320 of the outer sheath assembly 300 has come to rest against the keys 430 and 440. Thus, the outer sheath assembly 300 is decocked and has been fired.

Beginning with the state of the insertion device 100 illustrated in FIGS. 7A and 7B, in which the insertion device 100 is decocked and post firing, cocking of the insertion device 100 and placing the insertion device 100 into the position for insertion and the position for firing are now described. The insertion device 100 is moved from the decocked state, post-firing position to the cocked state, insertion position by pulling the base plate 470 away from the distal end 101 of the insertion device 200. As the base plate 470 moves away from the distal end 101 of the insertion device 200, the keys 440 and 450 of the biopsy needle assembly 400, which abut the proximal stop surface 324, pull the body 310 of the outer sheath assembly 300 into the trigger housing 200. The resilient member 600 is thereby compressed. The outer sheath assembly 300 stops moving toward the proximal end 102 of the insertion device 100 when the tabs 233 and 243 fall into the slots 333 and 343 and, optionally, the proximal end 312 of the body 310 comes into contact with the at least one inwardly projecting stop surface 221. At that point, the insertion device 100 is cocked, and the base plate 470 is separated from the trigger housing 200 at such a distance that the arms 450 and 460 are not disposed within their respective channels 250 and 260. After the insertion device 100 is cocked, it may be placed into the position for firing or the position for insertion.

To place it into the position for firing, the base plate 470 is moved toward the distal end 101 of the insertion device 100 to place it in the position for firing illustrated in FIGS. 1A and 1B. In this position, the biopsy needle assembly 400 is in a rotational position X, and the keys 430 and 440 are disposed near the distal end 321 of the interior channel 320.

To place the insertion device 100 into the position for insertion, if the base plate 470 is not at a distance from the distal end 101 of the insertion device 100, the base plate 470 may be separated from the trigger housing 200 at such a distance that the arms 450 and 460 are not disposed within their respective channels 250 and 260. Such movement does not result in the outer sheath assembly 300 moving as the keys 430 and 440 have room in the interior channel 320 to move toward the proximal end 322 thereof in the cocked state of the insertion device 100. After the arms 450 and 460 clear their respective channels 250 and 260, the base plate 470 may be rotated 90 degrees and moved toward the distal end 101 of the insertion device 100 to place it in the position for insertion illustrated in FIGS. 6A and 6B. In this position, the biopsy needle assembly 400 is in a rotational position Y, and the keys 430 and 440 are disposed in a midpoint of the interior channel 320. Alternatively, after the arms 450 and 460 clear their respective channels 250 and 260, the base plate 470 may be rotated 90 degrees, and the biopsy needle device 400 may withdrawn from the insertion device 100 by moving the biopsy needle device 400 away from the distal end 101 of the insertion device 100. When in this rotational position Y, the biopsy needle assembly 400 may be removed because the key 440 is aligned with the keyway 314B, and the key 430 is aligned with the keyway 314C. The needle 500 for taking an FNA sample may then be inserted into the insertion device 100 via the proximal opening 214 and through the inner lumen 384 of the outer sheath 380.

Moving the insertion device 100 from the insertion position to the firing position and back again is accomplished by moving the base plate 470 away from the distal end 101 of the insertion device 100, rotating the base plate 470 90 degrees, and then moving the base plate 470 toward the distal end 101 of the insertion device 100. When the insertion device 100 is in the cocked state and the position for firing, the insertion device 100 is fired by pressing the base plate 470 toward the distal end 101 of the insertion device 100.

During firing, the medical practitioner presses the base plate 470 against the trigger housing 200 while maintaining a grasp on the trigger housing 200. The push surfaces 436 and 446 of the respective arms 450 and 460 press against the respective trigger/press surfaces 236 and 246. Because the push surfaces 436 and 446 are angled inwardly toward the interior channel 220, they press the trigger/press surfaces 236 and 246 toward one another. This motion causes the release rockers 230 and 240 to rotate so that the tabs 233 and 243 move outwardly away from the interior channel 220. The tabs 233 and 243 leave their respective slots 333 and 343, i.e., the rockers 230 and 240 move or rotate by a predetermined amount determined by the lengths of the tabs 233 and 243 residing within the respective slots 333 and 343. Once they do so, the force resisting the expansion of the compressed resilient member 600 disappears, and the resilient member 600 forces the outer sheath assembly 300 away from the proximal end 202 of the trigger housing 200. The outer sheath 380, therefore, snaps over the notch 484 of the biopsy needle 480, and any tissue residing within the notch 484 is sheared off. The body 310 stops moving away from the proximal end 202 of the trigger housing 200 when the keys 430 and 440 disposed on the sliding mount 410 stop against the proximal stop surface 324 of the internal channel 320 of the outer sheath assembly 300. FIGS. 7A and 7B illustrate the insertion device 100 after the outer sheath assembly 300 has been fired.

As discussed above, in the rotational position X, the keys 430 and 440 of the biopsy needle assembly 400 are rotated 90 degrees with respect to the keyways 318B and 318C. Thus, in this position, the biopsy needle assembly 400 may not be removed from the outer sheath assembly 300 or the trigger housing 200. In the rotational position Y, the keys 430 and 440 are aligned with the keyways 318B and 318C. Thus, in this position, the biopsy needle assembly 400 may be removed from the outer sheath assembly 300.

The biopsy needle assembly 400 is removable from the trigger housing 200 and the outer sheath assembly 300 to facilitate further biopsies to be taken using the biopsy needle assembly 400 or other sterile biopsy needle assemblies constructed similarly to the biopsy needle assembly 400 or for fine needle aspiration using the FNA needle 500. Thus, the insertion device 100 allows the medical practitioner to take multiple core samples using biopsy needle assemblies 400 and multiple FNAs using the FNAs needles 500 without being required to remove the outer sheath assembly 300 from the area in a patient to be sampled. Thus, the patient is not subject to multiple needle sticks when multiple samples are taken.

As described above, the biopsy needle assembly 400 is withdrawn from the insertion device when it is in a cocked state. Withdrawal of the biopsy needle assembly 400 does not result in the outer sheath assembly 300 firing. Rather, the motion required for withdrawing the biopsy needle assembly 400 begins with cocking the device 100. Further, when the biopsy needle assembly 400 is in rotational position Y for removing it from the insertion device 100, the insertion device 100 cannot be fired by the biopsy needle assembly 400 because the arms 450 and 460 are not disposed within their respective channels 250 and 260. Thus, the risks of inadvertent firing of the insertion device 100 are substantially lower than that of the conventional device 1000.

The risks of inadvertent firing of the insertion device 100 by direct pressing of the release rockers 230 and 240 are reduced because the connectors 231, 232, 241, and 242 are generally centered within the indentations 234 and 244 of the respective release rockers 230 and 240. Inadvertent firing of the insertion device 100 may also be reduced by altering features of the release rockers 230 and 240 of the trigger housing 200 and the arms 450 and 460 of the biopsy needle assembly 400. For example, in an exemplary alternative embodiment of the insertion device 100, the trigger/press surfaces 236 and 246 may be altered to angle inwardly, so that they are pulled outwardly to remove the tabs 233 and 243 from their respective slots 333 and 343. Such pulling may be achieved by altering the push surfaces 436 and 446 of the respective arms 450 and 460 to angle outwardly and to relocate the tabs 233 and 243 to the proximal ends of the release rockers 230 and 240. In a variation on such alternative exemplary embodiment, the release rockers 230 and 240 may be further altered so that their connections to the body 210 are located at the distal ends of the release rockers 230 and 240.

Figure 9A:
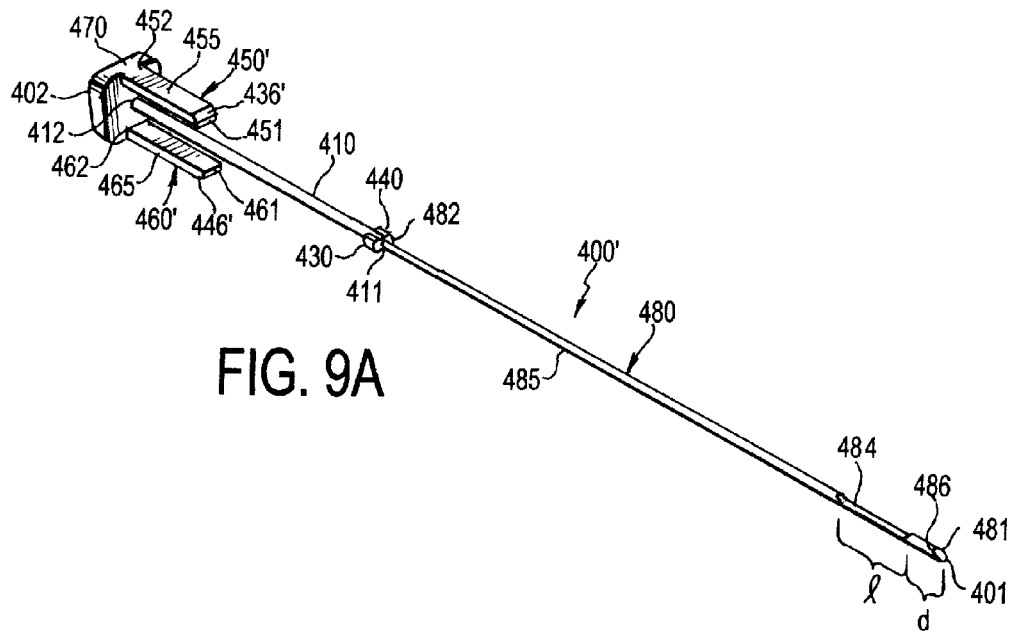
FIG. 9A illustrates a perspective view of another embodiment of the biopsy needle assembly of FIG. 1, in accordance with an exemplary embodiment of the present invention.
Figure 9B:
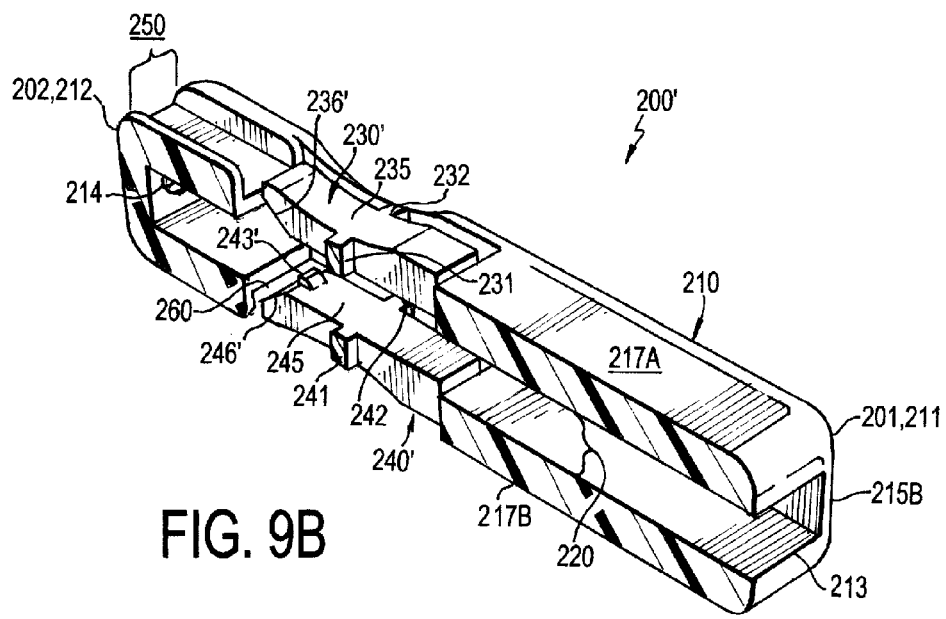
FIGS. 9B-9D illustrate perspective views of cross-sections of other embodiments of the trigger housing taken along an axis offset from a line corresponding to the line A-A of FIG. 1A, in accordance with an exemplary embodiment of the present invention.

Illustrated in FIG. 9A is an exemplary alternative embodiment of the biopsy needle assembly 400, generally designated as 400' in the figure, in accordance with an exemplary embodiment of the present invention. Illustrated in FIG. 9B is an exemplary alternative embodiment of the trigger housing 200, generally designated in the figure as 200' and shown in a cross section taken along an axis offset from a line corresponding to the line A-A of FIG. 1A, in accordance with an exemplary embodiment of the present invention. The trigger housing 200' and the biopsy needle assembly 400' are used in an exemplary alternative embodiment of the insertion device 100.

Referring to FIGS. 9A and 9B, the biopsy needle assembly 400' comprises arms 450' and 460', which correspond to the arms 450 and 460 of the biopsy needle assembly 400. The arms 450' and 460', however, respectively comprise outwardly facing push surface 436' and 446', rather than the inwardly facing push surfaces 436 and 446 of the respective arms 450 and 460. Thus, the orientation of the push surfaces 436' and 446' of the arms 450' and 460' differ from the push surfaces 436 and 446 of the arms 450 and 460.

The trigger housing 200' comprises rockers 230' and 240', which correspond to the rockers 230 and 240 of the trigger housing 200. The rockers 230' and 240', however, respectively comprise inwardly facing trigger/press surfaces 236' and 246'. The trigger/press surface 236' is configured for engaging the outwardly facing push surface 436' of the biopsy needle assembly 400' during firing, and the trigger/press surface 246' is configured for engaging the outwardly facing push surface 446' of the biopsy needle assembly 400' during firing. Thus, the orientation of the trigger/press surfaces 236' and 246' of the rockers 230' and 240' differ from the trigger/press surfaces 236 and 246 of the rockers 230 and 240.

The rockers 230' and 240' respectively comprise tabs 233' (not illustrated) and 243' disposed on the proximal ends of the rockers 230' and 240', rather than being located in the middle, as the tabs 233 and 243 of the rockers 230 and 240 are. Like the tabs 233 and 243, the tabs 233' and 243' serve to cock (releasably lock) the outer sheath assembly 300 with respect to the trigger housing 200. Thus, the tab 233' of the release rocker 230' extends within the slot 333, and the tab 243' of the release rocker 240' extends within the slot 343, when the outer sheath assembly 300 is cocked in position for firing.

In this exemplary alternative embodiment of the insertion device 100, the insertion device 100 operates and may be operated as described above. Firing of the exemplary alternative embodiment of the insertion device 100 incorporating the trigger housing 200' differs slightly from the firing described above because of the modified trigger/press surfaces 236' and 246' and push surfaces 436' and 446' and the relocated tabs 233' and 243'. During firing, the push surfaces 436' and 446' of the respective arms 450' and 460' press against the respective trigger/press surfaces 236' and 246'. Because the push surfaces 436' and 446' are angled outwardly away from the interior channel 220, they press the trigger/press surfaces 236' and 246' away from one another. This motion causes the release rockers 230' and 240' to rotate so that the tabs 233' and 243' move outwardly away from the interior channel 220. The tabs 233' and 243' leave their respective slots 333 and 343, and the exemplary alternative embodiment of the insertion device 100 fires. Because the tabs 233' and 243' are relocated in this exemplary alternative embodiment, it is to be understood that the body 310 of the outer sheath assembly 300 may be lengthened or adjusted to accommodate the relocated positions of the tabs 233' and 243'.

Figure 9C:
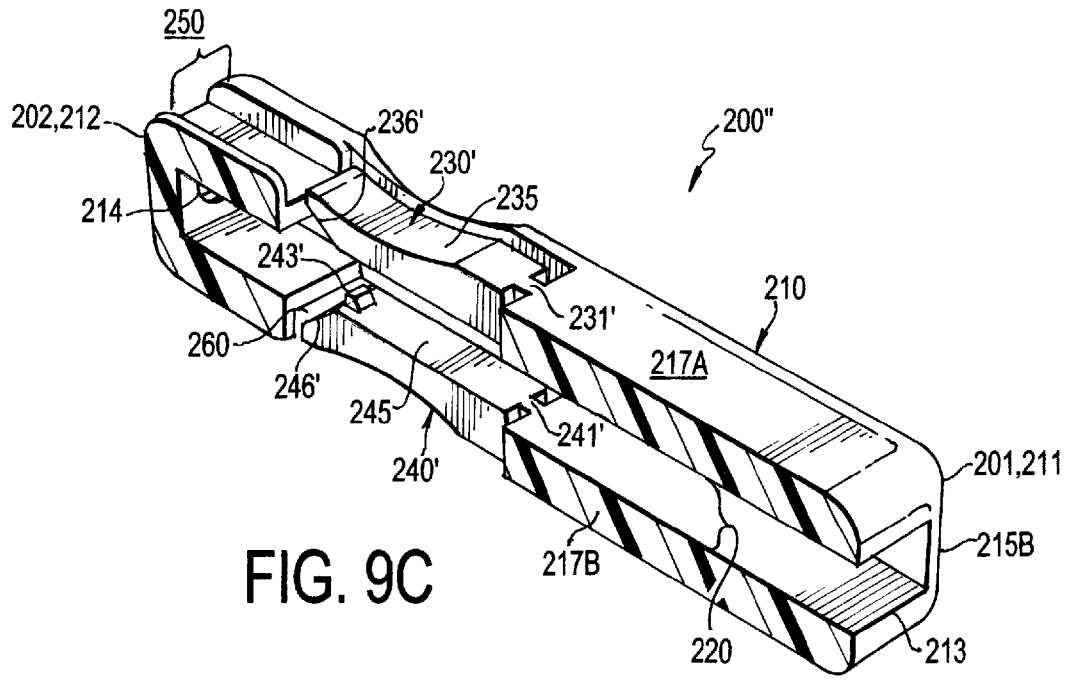

Referring now to FIG. 9C, there is illustrated another exemplary alternative embodiment of the trigger housing 200, generally designated in the figure as 200" and shown in a cross section taken along an axis offset from a line corresponding to the line A-A of FIG. 1A, in accordance with an exemplary embodiment of the present invention. The trigger housing 200" is similar to the trigger housing 200' but differs in that the connectors 231, 232, 241, and 242 have been removed. Instead, the release rocker 230' is connected at its distal end to the body 210 by a connector 231', and the release rocker 240' is connected at its distal end to the body 210 by a connector 241'. The release rockers 230' and 240' therefore act as release levers, as they pivot about their distal ends. The trigger housing 200" may be incorporated into the exemplary alternative embodiment of the insertion device 100 described above with respect to FIGS. 9A and 9B and operated as described above. As with FIGS. 9A and 9B, it is to be understood that the body 310 of the outer sheath assembly 300 may be lengthened or adjusted in the exemplary alternative embodiment of the insertion device 100 incorporating the trigger housing 200". Further, although the tab 243' is illustrated in FIG. 9C as being disposed on the release rocker 240' at its proximal end, it is to be understood that the tabs 233' and 243' may be disposed on the respective release rockers 230' and 240' at their midpoints or at other positions and that the body 310 of the out sheath assembly 300 may be lengthened or adjusted as desired.

Figure 9D:
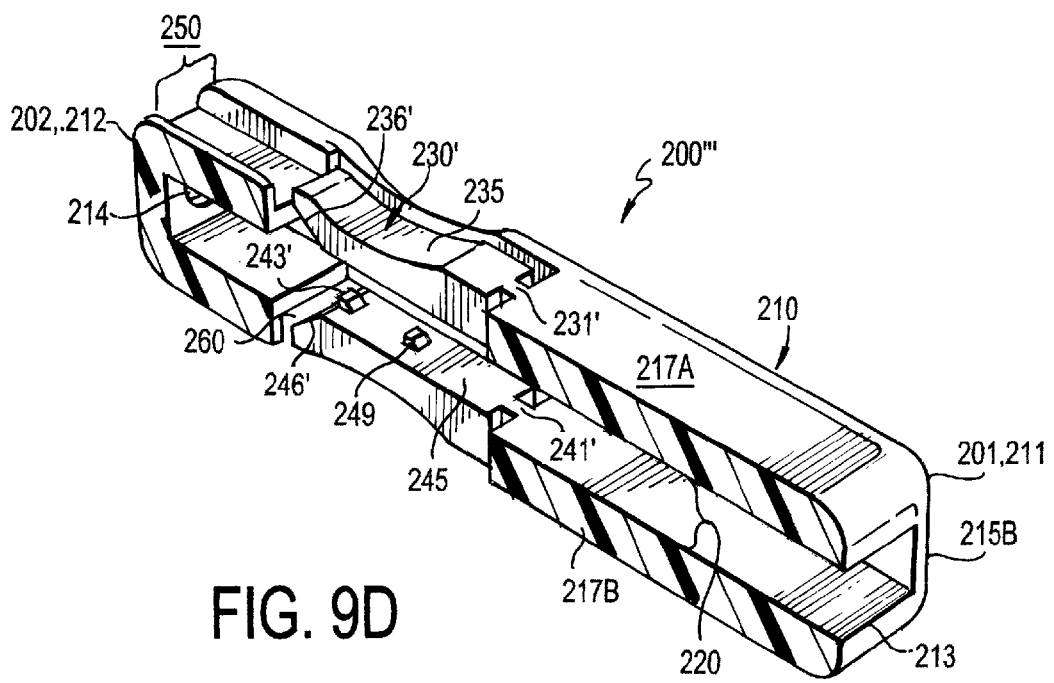

Referring now to FIG. 9D, there is illustrated yet another exemplary alternative embodiment of the trigger housing 200, generally designated in the figure as 200' and shown in a cross section taken along an axis offset from a line corresponding to the line A-A of FIG. 1A, in accordance with an exemplary embodiment of the present invention. The trigger housing 200'" is similar to the trigger housing 200" but differs in that in that it includes an additional pair of tabs 239 (not illustrated) and 249 disposed, respectively, on the release rockers 230' and 240'. Thus, each release rocker 230' and 240' comprises two tabs to provide for selection between two differently sized core samples. For example, the tabs 239 and 249 may be located to provide for a 10 mm core sample, and the tabs 233' and 243' may be located to provide for a 20 mm core sample. It is to be understood that the body 310 of the outer sheath assembly 300 may be lengthened or adjusted in the exemplary alternative embodiment of the insertion device 100 incorporating the trigger housing 200'. Further, it is to be understood that the body 310 of the outer sheath assembly 300 may be altered to provide for an additional pair of slots to engage with the tabs 239 and 249.

The trigger housing 200'" may be incorporated into the exemplary alternative embodiment of the insertion device 100 described above with respect to FIGS. 9A and 9B and operates and may be operated as described above. Cocking of the modified insertion device 100 incorporating the trigger housing 200' differs from the cocking of the insertion device 100 described above because the additional tabs 239 and 249 provide for a second size of core sample. When cocked for a 10 mm core sample, the slots 333 and 343 are engaged, respectively, with the tabs 239 and 249. The tabs 233' and 243' are not engaged with any slots, and the additional slots of the altered body 310 are not engaged with any tabs. When cocked for a 20 mm core sample, the slots 333 and 343 are engaged, respectively, with the tabs 233' and 243' and the additional slots of the altered body 310 are engaged, respectively, with the tabs 239 and 249. Firing of the modified insertion device 100 incorporating the trigger housing 200'" is as described above. It is to be understood that the placement of the tabs 233', 243', 239, and 249 are not limited to providing for 10 mm and 20 mm core samples and that other placements for providing other sized core samples are contemplated. Further, additional pairs of tabs are contemplated for providing for more than two sizes of core samples.

The modified insertion device 100 incorporating the trigger housing 200'" may be used to obtain two differently sized core samples with one biopsy needle assembly 400' having one notch 484 of a length 1. When cocked for a 10 mm core sample, the outer sheath 380 of the outer sheath assembly 300 exposes only 10 mm of the notch 484 to provide for a 10 mm sample. When cocked for a 20 mm core sample, the outer sheath 380 of the outer sheath assembly 300 exposes 20 mm of the notch 484 to provide for a 20 mm sample. It is contemplated, however, that biopsy needle assemblies 400' having differently sized notches 484 may be used for obtaining the differently sized core samples in conjunction with the modified insertion device 100 incorporating the trigger housing 200'. The biopsy needle assembly 400' is removable and replaceable by the FNA needle assembly 500.

An exemplary method of using the insertion device 100 for taking core biopsy and FNA samples is now described with reference to FIGS. 8A through 8H, in accordance with an exemplary embodiment of the present invention. FIGS. 8A through 8H illustrate various steps S1-S8 of the exemplary method. It is to be understood that any of the exemplary embodiments of the insertion device 100 may be used in performing the steps S1-S8.

Referring now to FIG. 8A, the insertion device 100 has been cocked by pulling back the base plate 470 so that the tabs 233 and 243 have snapped into the slots 333 and 343 of the body 310 of the outer sheath assembly 300. The biopsy needle assembly 400 has also been rotated to the rotational position Y so that the insertion device 100 is ready for insertion, as illustrated in FIG. 8A, Step S1.

The medical practitioner inserts the beveled tip 486 of the biopsy needle 480 and the outer sheath 380 of the outer sheath assembly 300 into a patient 800 and, specifically, into the skin 810 of the patient 800 for the purposes of sampling a mass 820 and tissue 830 surrounding the mass 820, as illustrated in FIG. 8B, Step S2. After the insertion device 100 has been inserted, the medical practitioner pulls the base plate 470 away from the distal end 101 of the insertion device 100 to remove the biopsy needle assembly 400 from the insertion device 100 while leaving the outer sheath 380 of the outer sheath assembly 300 within the patient 800, as illustrated in FIG. 8C, Step S3. The insertion device 100 remains in the cocked state ready for firing.

The medical practitioner inserts the FNA needle 500 through the cannula 382 of the outer sheath 380 so that the distal tip 501 of the FNA needle 500 is located in a place of interest, such as the mass 820 or the surrounding tissue 830, Step S4. The medical practitioner obtains a sample from the patient 800 via the proximal end 502 of the FNA needle 500 and removes the FNA needle 500, leaving the cannula 382 of the outer sheath 380 in the patient 800, as illustrated in FIG. 8E, Step S5. The practitioner removes the FNA needle 500 by pulling it away from the distal end 101 of the insertion device 100.

The medical practitioner reinserts the biopsy needle assembly 400 into the insertion device 100 by inserting it through the proximal opening 214 in the rotational position Y. When the biopsy needle assembly 400 is inserted, the medical practitioner rotates the biopsy needle assembly 400 to the rotational position X and continues pressing the plate 470 toward the distal end 101 so that the arms 450 and 460 of the biopsy needle assembly 400 enter the channels 250 and 260. The medical practitioner continues pressing the biopsy needle assembly 400 until the push surfaces 436 and 446 are placed into contact with the trigger/press surfaces 236 and 246, as illustrated in FIG. 8F, Step S6.

A final press of the plate 470 toward the distal end 101 of the insertion device 100 causes the insertion device 100 to fire, as illustrated in FIG. 8G, Step S7. The outer sheath assembly 300 snaps towards the distal end 101 of the insertion device 100 until the proximal stop surface 324 comes to rest against the keys 430 and 440. The bevel 386 of the outer sheath 380 shears off the portion of the mass 820 or the tissue 830 that is caught within the notch 484 of the biopsy needle 480. The biopsy needle assembly 400 may then be withdrawn from the insertion device 100, as illustrated in FIG. 8H, Step S8, for additional biopsies or FNA. After sampling is complete, the medical practitioner removes the insertion device 100 from the patient 800.

These and other advantages of the present invention will be apparent to those skilled in the art from the foregoing specification. Accordingly, it is to be recognized by those skilled in the art that changes or modifications may be made to the above-described embodiments without departing from the broad inventive concepts of the invention. It is to be understood that this invention is not limited to the particular embodiments described herein, but is intended to include all changes and modifications that are within the scope and spirit of the invention.

What is claimed is:

1. An insertion device for taking samples within a body, the insertion device comprising:
    a trigger housing comprising a proximal end, a distal end, and an interior channel;
    an outer sheath assembly, at least a portion of which is slidably disposed within the interior channel of the trigger housing, the outer sheath assembly comprising:
        a body of the outer sheath assembly having a proximal end, a distal end, and an opening in the proximal end; and
        an outer sheath attached to the distal end of the body of the outer sheath assembly; and
    a trigger body disposed on the trigger housing;
    a resilient member disposed within the interior channel of the trigger housing, the resilient member configured to urge the outer sheath assembly away from the proximal end of the trigger housing when the trigger body is actuated; and
    a sampling assembly inserted into the outer sheath assembly, wherein:
        the sampling assembly comprises at least one of a biopsy needle assembly and a fine needle aspiration ("FNA") needle, wherein a portion of a proximal end of the biopsy needle assembly and a portion of a proximal end of the FNA needle are configured to obtain a sample,
        the biopsy needle assembly is a removable biopsy needle assembly comprising a proximal end, a distal end, and at least one key, and at least a portion of the removable biopsy needle assembly is removably disposed within the outer sheath assembly through the body of the outer sheath assembly, the opening in the proximal end of the body of the outer sheath assembly, and the outer sheath of the outer sheath assembly, and
        the opening in the proximal end of the body of the outer sheath assembly comprises at least one keyway to allow the at least one key of the biopsy needle assembly to pass therethrough when the biopsy needle assembly is in a first rotational position and to block the at least one key from passing therethrough when the biopsy needle assembly is in a second rotational position.

2. The insertion device of claim 1, wherein the trigger body further comprises at least one rocker configured to releasably engage the body of the outer sheath assembly.

3. The insertion device of claim 2, wherein the resilient member is configured to move the outer sheath assembly away from the proximal end of the trigger housing when the at least one rocker disengages from the body of the outer sheath assembly.

4. The insertion device of claim 2, wherein the at least one rocker is configured to releasably disengage from the body of the outer sheath assembly when the at least one rocker moves by a predetermined amount.

5. The insertion device of claim 2, wherein:
    the at least one rocker comprises at least one tab projecting inwardly into the interior channel of the trigger housing, the body of the outer sheath assembly comprises at least one recess, and
    the at least one tab is configured to releasably engage the at least one recess when the insertion device is cocked so that the at least one rocker releasably engages the body of the outer sheath assembly.

6. The insertion device of claim 1, wherein the body of the outer sheath assembly is the portion of the outer sheath assembly which is slidably disposed within the interior channel of the trigger housing.

7. An insertion device for taking samples within a body, the insertion device comprising:
    a trigger housing comprising a proximal end, a distal end, and an interior channel;
    an outer sheath assembly, at least a portion of which is slidably disposed within the interior channel of the trigger housing, the outer sheath assembly comprising:
        a body of the outer sheath assembly having a proximal end, a distal end, and an opening in the proximal end; and
        an outer sheath attached to the distal end of the body of the outer sheath assembly;
    a removable biopsy needle assembly having a proximal end and a distal end, at least a portion of the removable biopsy needle assembly is removably disposed within the outer sheath assembly through the body of the outer sheath assembly, the opening in the proximal end of the body of the outer sheath assembly, and the outer sheath of the outer sheath assembly;
    a trigger body disposed on the trigger housing; and
    a resilient member disposed within the interior channel of the trigger housing, the resilient member configured to urge the outer sheath assembly away from the proximal end of the trigger housing when the trigger body is actuated,
    wherein the insertion device is capable of receiving at least one of the removable biopsy needle assembly and a Fine Needle Aspiration ("FNA") needle, wherein a portion of a proximal end of the removable biopsy needle assembly and a portion of a proximal end of the FNA needle are configured to obtain a sample,
    wherein the removable biopsy needle assembly comprises at least one key, and
    wherein the opening in the proximal end of the body of the outer sheath assembly comprises at least one keyway configured to allow the at least one key to pass therethrough when the removable biopsy needle assembly is in a first rotational position and to block the at least one key from passing therethrough when the removable biopsy needle assembly is in a second rotational position.

8. The insertion device of claim 7, wherein the removable biopsy needle assembly comprises:
   a sliding mount comprising a proximal end and a distal end, the sliding mount removably disposed through the opening in the proximal end of the body of the outer sheath assembly; and
   a biopsy needle attached to the distal end of the sliding mount, the biopsy needle removably disposed through the outer sheath of the outer sheath assembly.

9. The insertion device of claim 8, wherein:
   the removable biopsy needle assembly further comprises at least one key disposed on the sliding mount, and the at least one key is configured to engage the proximal end of the body of the outer sheath assembly to cock the insertion device when the biopsy needle assembly is moved away from the distal end of the trigger housing.

10. The insertion device of claim 9, wherein:
    the opening in the proximal end of the body of the outer sheath assembly comprises at least one keyway corresponding to the at least one key disposed on the sliding mount of the removable inner biopsy needle assembly, and
    the removable biopsy needle assembly is rotatable within the insertion device between a first rotational position in which the at least one key disposed on the sliding mount is aligned with the at least one keyway to pass therethrough, thereby allowing the removable biopsy needle assembly to be removed from the insertion device, and a second rotational position in which the at least one key disposed on the sliding mount is not aligned with the at least one keyway, thereby preventing the removable biopsy needle assembly from being removed from the insertion device.

11. The insertion device of claim 7, wherein the trigger body further comprises at least one rocker configured to releasably engage the body of the outer sheath assembly.

12. The insertion device of claim 11, wherein the resilient member is configured to move the outer sheath assembly away from the proximal end of the trigger housing when the at least one rocker disengages from the body of the outer sheath assembly.

13. The insertion device of claim 11, wherein the removable biopsy needle assembly further comprises a cap at the proximal end of the removable biopsy needle assembly, the cap comprising at least one arm configured to engage the proximal end of the trigger housing when the removable biopsy needle assembly is in a first rotational position and to engage the at least one rocker when the removable biopsy needle assembly is in a second rotational position.

14. The insertion device of claim 13, wherein the at least one arm causes the at least one rocker configured to releasably disengage from the body of the outer sheath assembly when the removable biopsy needle assembly is moved toward the distal end of the insertion device to cause the at least one rocker to move by a predetermined amount.

15. The insertion device of claim 11, wherein:
    the at least one rocker comprises at least one tab projecting inwardly into the interior channel of the trigger housing,
    the body of the outer sheath assembly comprises at least one recess, and
    the at least one tab is configured to releasably engage the at least one recess when the insertion device is cocked so that the at least one rocker releasably engages the body of the outer sheath assembly.

16. The insertion device of claim 15, wherein:
    the removable biopsy needle assembly further comprises a cap at the proximal end of the removable biopsy needle assembly, the cap comprising at least one arm configured to engage the proximal end of the trigger housing when the removable biopsy needle assembly is in a first rotational position and to engage the at least one rocker when the removable biopsy needle assembly is in a second rotational position, and
    the at least one arm causes the at least one tab to disengage from the at least one recess so that the at least one rocker disengages from the body of the outer sheath assembly, thereby allowing the resilient member to move the outer sheath assembly away from the proximal end of the trigger housing.

17. The insertion device of claim 7, wherein the body of the outer sheath assembly is the portion of the outer sheath assembly which is slidably disposed within the interior channel of the trigger housing.

18. The insertion device of claim 7, wherein the removable biopsy needle assembly is removable for replacement by a needle assembly for fine needle aspiration.

19. A method of inserting an insertion device into a body, the method comprising steps of:
    placing an insertion device in a first rotational position, the insertion device comprising:
      a trigger housing comprising a proximal end, a distal end, and an interior channel;
      an outer sheath assembly, at least a portion of which is slidably disposed within the interior channel of the trigger housing, the outer sheath assembly comprising:
        a body of the outer sheath assembly having a proximal end, a distal end, and an opening in the proximal end; and
        an outer sheath attached to the distal end of the body of the outer sheath assembly;
      a removable biopsy needle assembly having a proximal end and a distal end, at least a portion of the removable biopsy needle assembly is removably disposed within the outer sheath assembly through the body of the outer sheath assembly, the opening in the proximal end of the body of the outer sheath assembly, and the outer sheath of the outer sheath assembly; and
      a resilient member disposed within the interior channel of the trigger housing, the resilient member configured to urge the outer sheath assembly away from the proximal end of the trigger housing;
    inserting the insertion device into the body;
    placing the insertion device in a second rotational position after inserting the insertion device into the body, the placing the insertion device in the second rotational position further comprising placing the removable biopsy needle assembly in the second rotational position; and
    cocking the insertion device while in the second rotational position.

20. The method of claim 19, wherein the step of placing the insertion device in the first rotational position comprises placing the removable biopsy needle assembly in the first rotational position.

21. The method of claim 19, wherein:
    the removable biopsy needle assembly comprises at least one key, and the step of cocking the insertion device comprises pulling the removably biopsy needle assembly through opening in the proximal end of the body of the outer sheath assembly so that the at least one key pulls the outer sheath assembly toward the proximal end of the trigger housing.

22. The method of claim 21, wherein:

the trigger housing further comprises at least one rocker configured to releasably engage the body of the outer sheath assembly, and the step of cocking the insertion device further comprises pulling the removably biopsy needle assembly through opening in the proximal end of the body of the outer sheath assembly so that the at least one rocker engages the body of the outer sheath assembly.

23. The method of claim 22, wherein:

the at least one rocker comprises at least one tab projecting inwardly into the interior channel of the trigger housing, and the body of the outer sheath assembly comprises at least one recess, and the step of cocking the insertion device further comprises pulling the removably biopsy needle assembly through opening in the proximal end of the body of the outer sheath assembly so that the at least one tab of the at least one rocker engages the at least one recess of the body of the outer sheath assembly.

24. The method of claim 19, wherein:

the resilient member is a spring, and the step of cocking the insertion device compresses the spring.

* * * * *